US012590142B2

(12) United States Patent
Allison et al.

(10) Patent No.: US 12,590,142 B2
(45) Date of Patent: Mar. 31, 2026

(54) ANTIBODY PURIFICATION AND PURITY MONITORING

(71) Applicant: H. LUNDBECK A/S., Valby (DK)

(72) Inventors: Daniel S. Allison, Lake Forest Park, WA (US); Steven D. Davin, Seattle, WA (US); Hoa Binh Do, Kirkland, WA (US); Leon F. Garcia-Martinez, Woodinville, WA (US); Geoffrey F. Lee, Mercer Island, WA (US); Ethan W. Ojala, Snohomish, WA (US); Mark Young, Boulder, CO (US); John A. Latham, Seattle, WA (US)

(73) Assignee: H. LUNDBECK A/S, Valby (DK)

(*) Notice: Subject to any disclaimer, the term of this patent is extended or adjusted under 35 U.S.C. 154(b) by 0 days.

(21) Appl. No.: 16/739,724

(22) Filed: Jan. 10, 2020

(65) Prior Publication Data

US 2020/0223913 A1    Jul. 16, 2020

Related U.S. Application Data

(62) Division of application No. 15/331,241, filed on Oct. 21, 2016, now Pat. No. 10,533,045, which is a division of application No. 14/215,370, filed on Mar. 17, 2014, now Pat. No. 9,518,082.

(60) Provisional application No. 61/792,935, filed on Mar. 15, 2013.

(51) Int. Cl.
| | |
|---|---|
| C07K 16/00 | (2006.01) |
| B01D 15/32 | (2006.01) |
| B01D 15/38 | (2006.01) |
| B01D 15/42 | (2006.01) |
| C07K 1/16 | (2006.01) |
| C07K 1/20 | (2006.01) |
| C07K 1/22 | (2006.01) |
| C07K 1/34 | (2006.01) |
| C07K 1/36 | (2006.01) |
| C07K 16/06 | (2006.01) |
| C07K 16/18 | (2006.01) |
| G01N 33/68 | (2006.01) |

(52) U.S. Cl.
CPC ............ *C07K 16/18* (2013.01); *B01D 15/327* (2013.01); *B01D 15/3809* (2013.01); *B01D 15/424* (2013.01); *C07K 1/165* (2013.01); *C07K 1/20* (2013.01); *C07K 1/22* (2013.01); *C07K 1/34* (2013.01); *C07K 1/36* (2013.01); *C07K 16/065* (2013.01); *G01N 33/68* (2013.01); *G01N 33/6854* (2013.01); *C07K 2317/14* (2013.01); *C07K 2317/41* (2013.01); *C07K 2317/51* (2013.01); *C07K 2317/515* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 8,067,182 B2 | 11/2011 | Kelley et al. | |
| 9,518,082 B2 | 12/2016 | Allison et al. | |
| 9,745,373 B2* | 8/2017 | Kovacevich | ........... C07K 16/26 |
| 2010/0028947 A1 | 2/2010 | Goletz et al. | |
| 2010/0172911 A1 | 7/2010 | Naso et al. | |
| 2011/0117601 A1 | 5/2011 | Haberger et al. | |
| 2014/0072585 A1 | 3/2014 | Herigstad et al. | |
| 2014/0288278 A1 | 9/2014 | Nti-gyabaah et al. | |

FOREIGN PATENT DOCUMENTS

| | | |
|---|---|---|
| EP | 1614693 | 1/2006 |
| WO | 1995022389 | 8/1995 |
| WO | 2003042233 | 5/2003 |
| WO | 2004090549 | 10/2004 |
| WO | 2009027041 | 3/2009 |
| WO | 2011049798 | 4/2011 |
| WO | 2011146179 | 11/2011 |
| WO | 2013013193 | 1/2013 |
| WO | 2013028635 | 2/2013 |

OTHER PUBLICATIONS

Li et al., Nature Biotechnology, Feb. 2006, 24(2):210-215. (Year: 2006).*

Sutton C, et al. "Purification and sequencing of glycosylation variants of BSF-1, as a MAF, from the EL-4 leukaemia cell line," J Biol Stand. Jan. 1989;17(1):65-74.

Du, et al. "Chromatographic analysis of the acidic and basic species of recombinant monoclonal antibodies," MAbs. Sep.-Oct. 2012;4(5):578-85.

Horenstein, Alberto L et al. "Design and scaleup of downstream processing of monoclonal antibodies for cancer therapy: from research to clinical proof of principle." Journal of immunological methods vol. 275,1-2 (2003): 99-112. doi:10.1016/s0022-1759(03)00006-1.

* cited by examiner

*Primary Examiner* — Stacy B Chen
(74) *Attorney, Agent, or Firm* — Robin L. Teskin; Baker, Donelson, Bearman, Caldwell & Berkowitz PC

(57) ABSTRACT

Processes for producing and purifying recombinant proteins are disclosed. In particular, the present disclosure provides processes of producing and purifying multi-subunit proteins expressed in yeast or filamentous fungal cells. The production and/or purification of such proteins are monitored for impurities, preferably using lectin binding assays, such that one or more process parameters may be adjusted to maximize the amount of desired recombinant protein and minimize the amount of glycosylated impurities. The processes can also be monitored for other undesired product-associated impurities, such as aggregates and nucleic acids. In exemplary embodiments, the recombinant proteins are multi-subunit proteins, such as antibodies, the host cell is a yeast, such as *Pichia pastoris*, and the glycosylated impurity is a glycovariant of the desired recombinant polypeptide, such as an N-linked and/or O-linked glycovariant.

7 Claims, 13 Drawing Sheets

Specification includes a Sequence Listing.

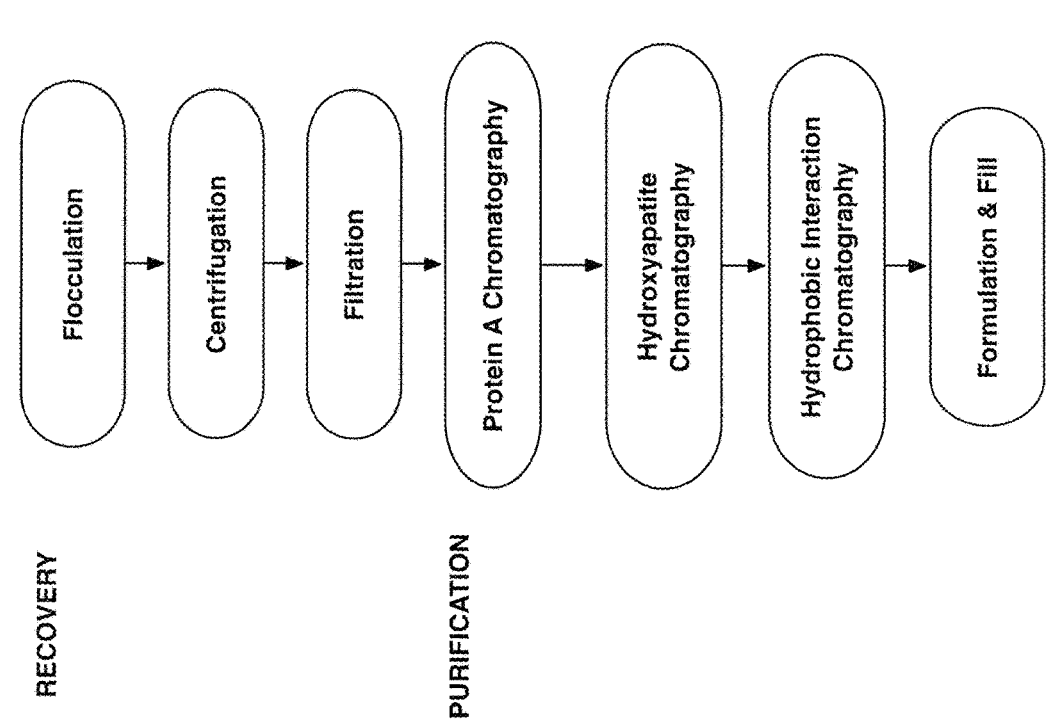
Fig 1. Overview of Purification Process

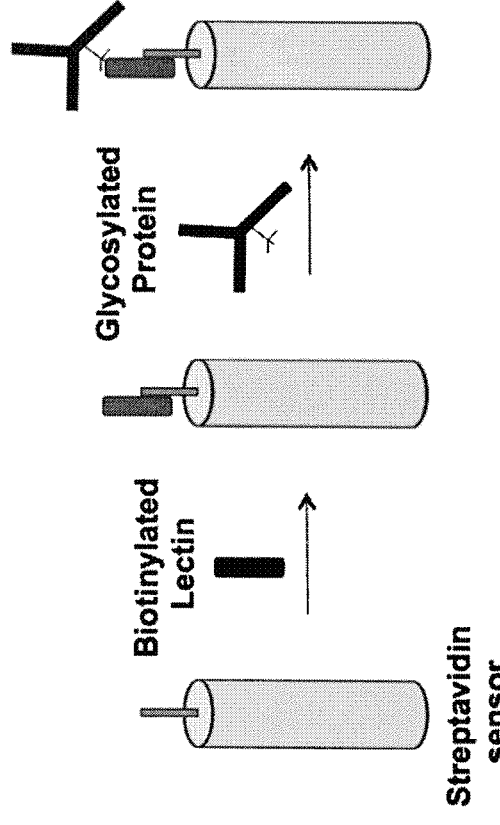
Fig 2. Monitoring glycosylation impurities using lectin.

Fig 3. Glycovariant impurities in Ab-A hydroxyapatite chromatography fractions.
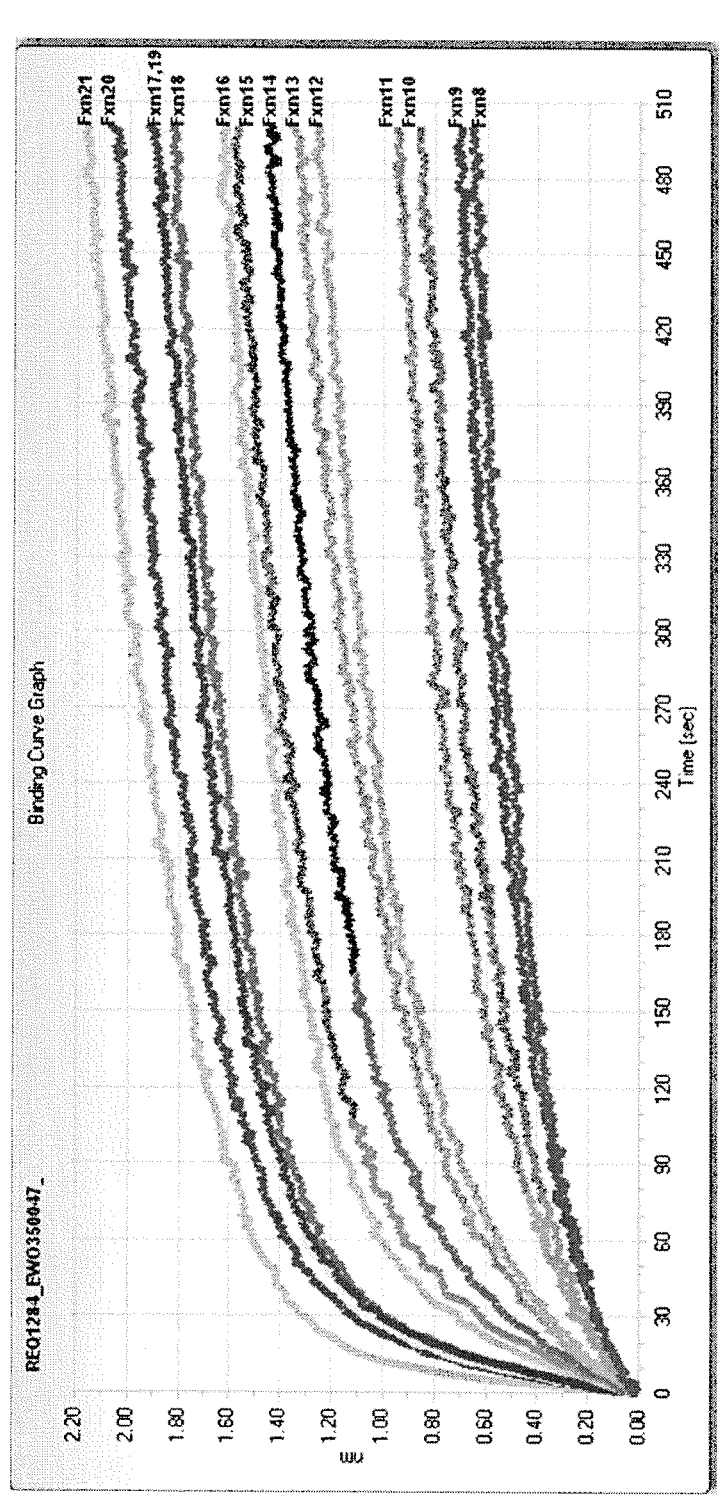

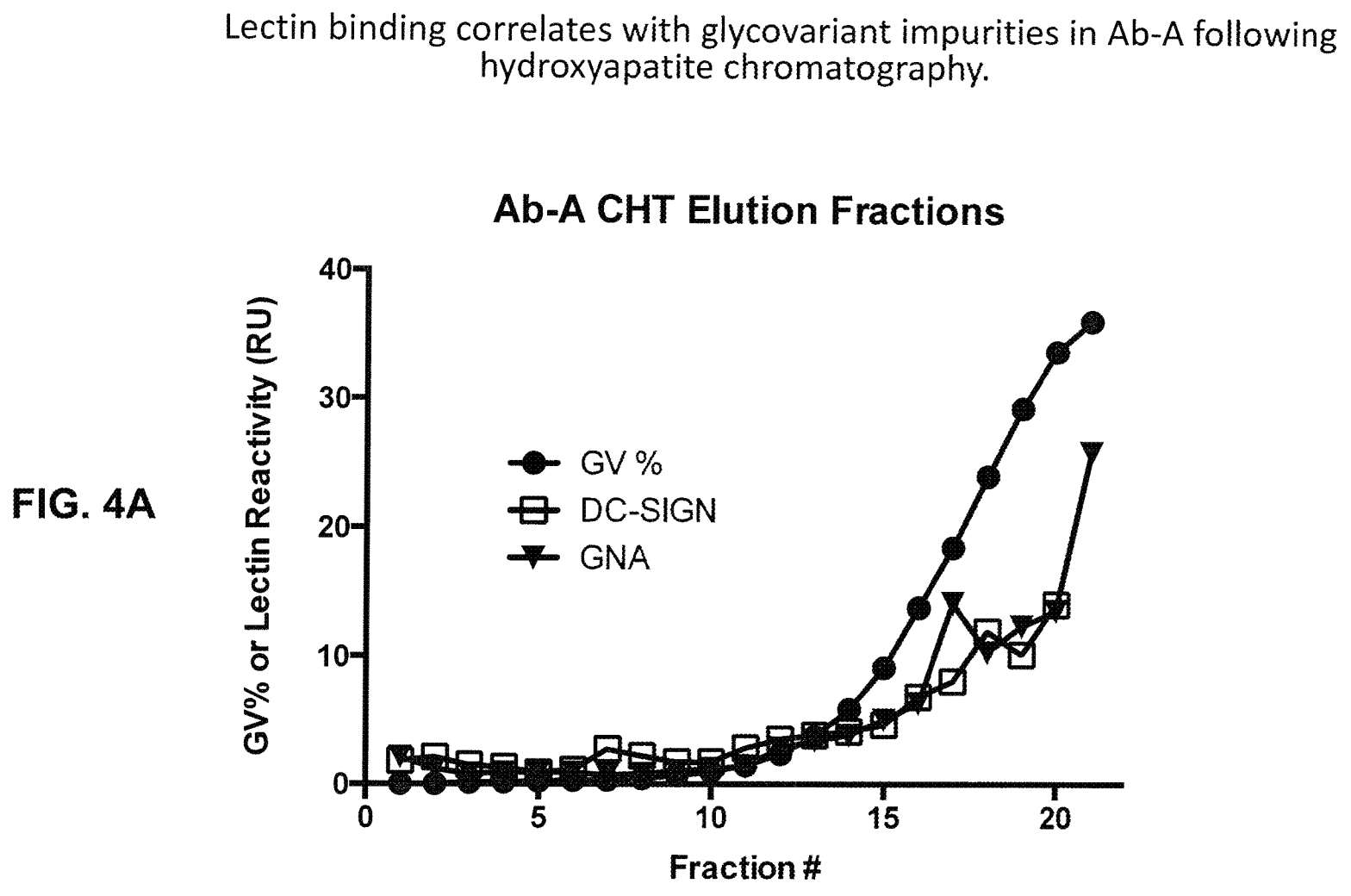

Lectin binding correlates with glycovariant impurities in Ab-A following hydroxyapatite chromatography.

Ab-A CHT Elution Fractions

FIG. 4A

Glycovariant impurities in Ab-A following hydroxyapatite chromatography.

FIG. 5B

SE-HPLC data:

|                 | 0.4% GV |
| --------------- | ------- |
| Baseline Pool   | 0.4% GV |
| Stringent Pool  | 0.1% GV |

O-glyco Analysis:

|                | Monomannose | Mannobiose | Mannotriose |
| -------------- | ----------- | ---------- | ----------- |
| Baseline Pool  | 1.60        | 0.28       | 0.28        |
| Stringent Pool | 1.55        | 0.28       | 0.22        |

GNA-Octet data:

|                |         |
| -------------- | ------- |
| Baseline Pool  | 2.3 RU  |
| Stringent Pool | 1.9 RU  |

Glycovariants in Ab-A following hydrophobic interaction chromatography.

FIG. 6B

SE-HPLC data:

Baseline Pool      0.4% GV

Stringent Pool      0.3% GV

O-glyco Analysis:

| | Monomannose | Mannobiose | Mannotriose |
|---|---|---|---|
| Baseline Pool | 1.57 | 0.52 | 0.32 |
| Stringent Pool | 1.48 | 0.14 | 0.07 |

GNA-Octet data:

Baseline Pool      1.4 RU

Stringent Pool      1.1 RU

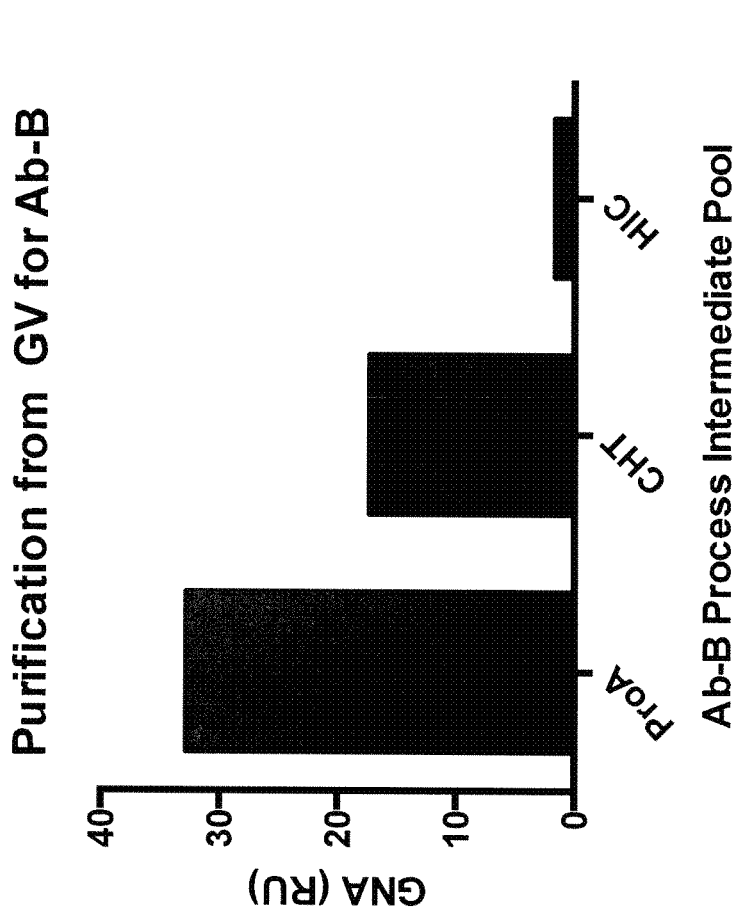
Fig 8. Glycovariant impurities in Ab-B during process.

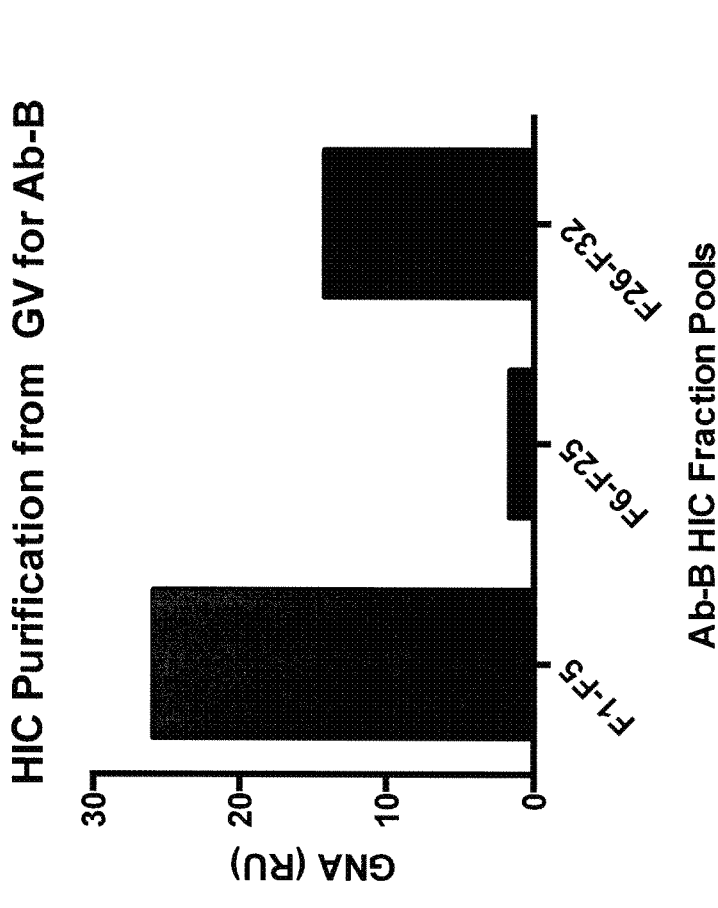
Fig 9. Glycovariants in Ab-B following hydrophobic interaction chromatography.

Fig 10. Ab-B purity.
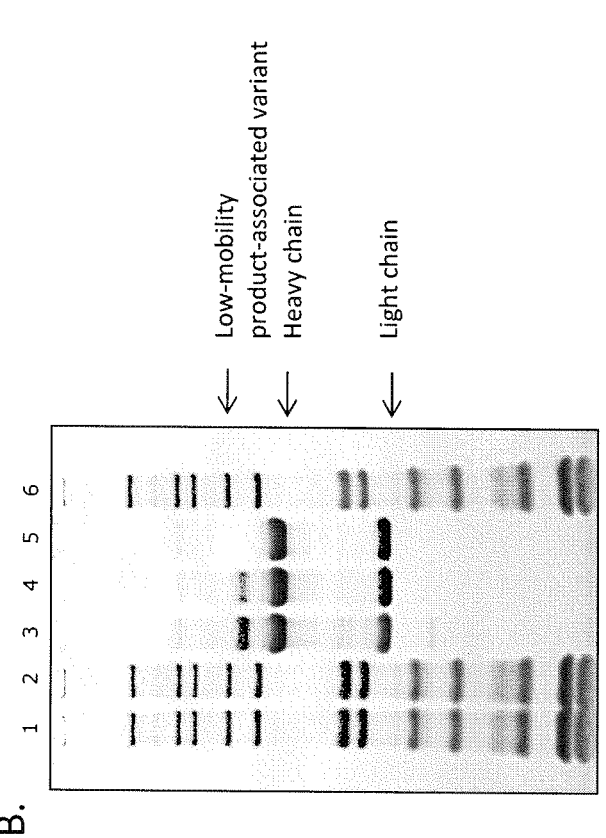
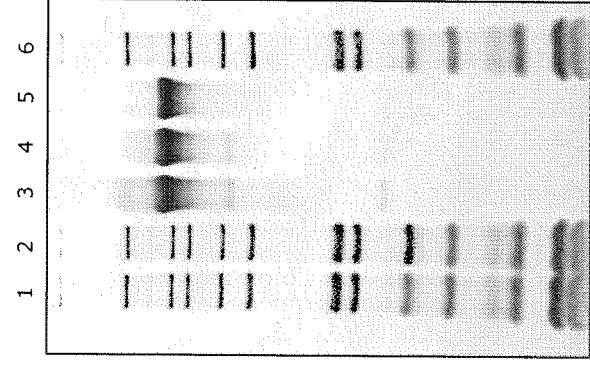

ANTIBODY PURIFICATION AND PURITY MONITORING

PRIORITY APPLICATION INFORMATION

This application is a divisional application of U.S. application Ser. No. 15/331,241, which is a divisional application of U.S. application Ser. No. 14/215,370 filed Mar. 17, 2014, which in turn claims priority to U.S. Provisional Application No. 61/792,935, filed Mar. 15, 2013, each and all of which are hereby incorporated by reference in their entirety herein.

SEQUENCE DISCLOSURE

The instant application contains a Sequence Listing, which has been submitted in ASCII format via EFS-Web and is hereby incorporated by reference in its entirety. The ASCII copy, created on Sep. 28, 2022, is named "1143257.003604.txt" and is 7,875 bytes in size.

FIELD OF INVENTION

The present disclosure generally relates to processes for producing and purifying recombinant polypeptides. In particular, the present disclosure provides processes of producing and purifying homopolymeric or heteropolymeric polypeptides expressed in yeast or filamentous fungal cells using lectin binding assays to monitor for glycosylated impurities. As a result, the fermentation process and/or the purification method may be adjusted to maximize the amount of desired recombinant protein and minimize the amount of glycosylated impurities and other undesired product-associated impurities, such as aggregates and nucleic acids. In exemplary embodiments, the recombinant proteins are multi-subunit proteins, such as antibodies, the host cell is a yeast, such as *Pichia pastoris*, and the glycosylated impurity is a glycovariant of the desired recombinant polypeptide, such as an N-linked and/or O-linked glycovariant.

BACKGROUND

Large-scale, economic purification of proteins is an increasingly important concern in the biotechnology industry. Generally, proteins are produced by cell culture using, prokaryotic, e.g., bacterial, or eukaryotic, e.g., mammalian or fungal, cell lines engineered to produce the protein of interest by insertion of a recombinant plasmid comprising the gene for that protein. Since the cell lines used are living organisms, they must be fed with a complex growth medium, comprising sugars, amino acids, and growth factors, sometimes supplied from preparations of animal serum. Separation of the desired recombinant protein from the mixture of compounds fed to the cells and from the by-products generated by the cells themselves to a purity sufficient for use as a human therapeutic poses a formidable challenge.

Multimeric, e.g., homopolymeric and heteropolymeric, proteins represent one of the most complex levels of structural organization in biological molecules. Not only do the constituent polypeptide chains have to fold (into secondary structures and tertiary domains) but they must also form complementary interfaces that allow stable subunit interactions. These interactions are highly specific and can be between identical subunits or between different subunits.

In particular, conventional antibodies are tetrameric proteins composed of two identical light chains and two identical heavy chains. Pure human antibodies of a specific type can be difficult to purify from natural sources in sufficient amounts for many purposes. As a consequence, biotechnology and pharmaceutical companies have turned to recombinant DNA-based methods to prepare antibodies on a large scale. Hundreds of therapeutic monoclonal antibodies (mAbs) are either currently on the market or under development. The production of functional antibodies (including antibody fragments that retain antigen-specificity and often display improved functionality and physico-chemical properties) generally involves the synthesis of the two polypeptides as well as a number of post-translational events, including proteolytic processing of the N-terminal secretion signal sequence; proper folding and assembly of the polypeptides into tetramers; formation of disulfide bonds; and typically includes a specific N-linked glycosylation.

Additionally, cytokines, as pleiotropic regulators that control proliferation, differentiation, and other cellular functions of immune and hematopoietic systems, have potential therapeutic use for a wide range of infectious and autoimmune diseases. Much like antibodies, recombinant expression methods are often used to express recombinant cytokines for subsequent use in research and pharmaceutical applications.

Recombinant synthesis of such proteins has typically relied on cultures of higher eukaryotic cells to produce biologically active material, with cultured mammalian cells being very commonly used. However, mammalian tissue culture-based production systems incur significant added expense and complication relative to microbial fermentation methods. Additionally, products derived from mammalian cell culture may require additional safety testing to ensure freedom from mammalian pathogens (including viruses) that might be present in the cultured cells or animal-derived products used in culture, such as serum.

Prior work has helped to establish the yeast *Pichia pastoris* as a cost-effective platform for producing functional antibodies that are potentially suitable for research, diagnostic, and therapeutic use. See co-owned U.S. Pat. Nos. 7,935,340; 7,927,863 and 8,268,582, each of which is incorporated by reference herein in its entirety. Methods are also known in the literature for design of *P. pastoris* fermentations for expression of recombinant proteins, with optimization having been described with respect to parameters including cell density, broth volume, substrate feed rate, and the length of each phase of the reaction. See Zhang et al., "Rational Design and Optimization of Fed-Batch and Continuous Fermentations" in Cregg, J. M., Ed., 2007. *Pichia* Protocols (2nd edition), Methods in Molecular Biology, vol. 389, Humana Press. Totowa, N.J., pgs. 43-63. See also, US 20130045888, entitled MULTI-COPY STRATEGY FOR HIGH-TITER AND HIGH-PURITY PRODUCTION OF MULTI-SUBUNIT PROTEINS SUCH AS ANTIBODIES IN TRANSFORMED MICROBES SUCH AS *PICHIA PASTORIS*; and US 20120277408, entitled HIGH-PURITY PRODUCTION OF MULTI-SUBUNIT PROTEINS SUCH AS ANTIBODIES IN TRANSFORMED MICROBES SUCH AS *PICHIA PASTORIS*.

Though recombinant proteins can be produced from cultured cells, undesired side-products may also be produced. For example, the cultured cells may produce the desired protein along with proteins having undesired or aberrant glycosylation. Additionally, cultured cells may produce multi-subunit protein along with free monomers and complexes having incorrect stoichiometry. Purification of the desired multi-subunit protein can increase production cost, and the steps involved in purification may decrease total yield of the desired complex. Moreover, even after purification, undesired side-products may be present in amounts that cause concern. For example, glycosylated side-products may be present in amounts that increase the risk of an immune reaction after administration, and may adversely affect properties such as stability, half-life, and specific activity, whereas aberrant complexes or aggregates may decrease specific activity and may also be potentially immunogenic.

SUMMARY

The invention provides a process for purifying a desired recombinant polypeptide from one or more samples resulting from a fermentation process that comprises culturing a desired cell or microbe under conditions that result in the expression and secretion of the recombinant polypeptide and one or more impurities into the fermentation medium; wherein the purification process includes detecting the amount and/or type of glycosylated impurities in the sample(s) using a lectin that binds to said glycosylated impurities, such as a glycovariant of the desired recombinant polypeptide resulting from, e.g., O-linked glycosylation and/or N-linked glycosylation.

In one embodiment, the purification process optionally further comprises contacting the sample(s) with at least one chromatographic support and selectively eluting the desired recombinant polypeptide, and detecting the amount and/or type of glycosylated impurities in the eluate or fractions thereof using a lectin that binds to said glycosylated impurities. The detection step can be effected using at least one lectin selected from ConA, LCH, GNA or GNL, RCA, DC-SIGN, L-SIGN, PNA, AIL, VVL, WGA, SNA, MAL, MAH, UEA and AAL. See Table 3. Preferably, the lectin is bound to a support. In one embodiment, the detection step uses a protein-protein interaction monitoring process, such as, but not limited to, light interferometry (ForteBio Octet®), dual polarization interferometry (Farfield AnaLight®), static light scattering (Wyatt DynaPro Nano-Stari™), dynamic light scattering (Wyatt DynaPro NanoS-tar™), multi-angle light scattering (Wyatt Calypso II), surface plasmon resonance (ProteOn XPR36 or Biacore T100), ELISA, chemiluminescent ELISA, far western, electro-chemiluminescence (such as that done using a MesoScale Discovery) or other lectin kinetic binding assay.

In one embodiment, the desired recombinant polypeptide is a homopolymeric or heteropolymeric polypeptide. Such homopolymeric or heteropolymeric recombinant polypeptides include, but are not limited to, hormones, growth factors, receptors (e.g., GPCRs and immune cell receptors), antibodies, cytokines, receptor ligands, transcription factors, toxins or enzymes. Non-limiting exemplary antibodies or antibody fragments include those that specifically bind to IL-2, IL-4, IL-6, IL-10. IL-12, IL-13, IL-17, IL-18. IFN-alpha. IFN-gamma, BAFF, CXCL13, IP-10, CBP, angiotensin (angiotensin I and angiotensin II), Nav1.7, Nav1.8, VEGF, PDGF, EPO, EGF, FSH, TSH, hCG, CGRP, NGF, TNF, HGF, BMP2. BMP7, PCSK9 or HRG. Preferably, the desired recombinant polypeptide is an antibody or an antibody fragment. In another embodiment, the antibody or antibody fragment is a human antibody or a humanized antibody or fragment thereof. The humanized antibody can be of mouse, rat, rabbit, goat, sheep, or cow origin. Preferably, the humanized antibody is of rabbit origin. In yet another embodiment, the antibody or antibody fragment comprises a monovalent, bivalent, or multivalent antibody.

In one embodiment, the desired recombinant polypeptide is expressed in a host cell that is a yeast or filamentous fungi. The yeast can be selected from *Arxiozyma; Ascoboloyma;*

*Citeromyces; Debaryomyces; Dekkera; Eremothecium; Issatchenkia; Kazachstania; Kluvveronmvces; Kodacm-raea; Lodderormyces; Pachysolen; Pichia; Saccharomyces; Saturnispora; Tetrapisispora; Torulaspora; Williopsis; Zvgosaccharomyces; Yarrowia; Rhodosporidiunm; Candida; Hansenula; Filobasium; Spxridiobolus; Bullera; Leu-cosporidium* and *Filobasidella*. Preferably, the yeast is *Pichia pastoris, Pichia angusta, Pichia guillermordii, Pichia melnaiolica,* or *Pichia inositovera*. More preferably, the yeast is *Pichia pastoris*. In a preferred embodiment the *Pichia pastoris* expresses an antibody or antibody fragment. The filamentous fungi can be selected from *Aspergillus, Tricholerma, Penicillium, Rhizopus, Paecilomyces, Fusarium, Neurospora* and *Claviceps*.

In one embodiment, the purification process includes chromatographic purification of the desired recombinant polypeptide comprising: (a) contacting the sample(s) with an affinity chromatographic support and separating the desired recombinant polypeptide from the support; (b) contacting the eluate or fraction thereof of step (a) with a mixed mode chromatographic support and selectively eluting the desired recombinant polypeptide from the support; and (c) contacting the eluate or fraction thereof of step (b) with a hydrophobic interaction chromatographic support and selectively eluting the desired recombinant polypeptide from the support, wherein the cluate or fraction thereof of step (c) comprises substantially purified desired recombinant polypeptide. In one embodiment, the affinity chromatographic support comprises an immunoaffinity ligand, such as Protein A, e.g., MabSelect SuRe, or lectin. e.g., GNL or DC-SIGN. A buffer comprising about 1 M arginine, pH 4.0 can be applied to the chromatographic support to elute the desired multi-subunit complex. In another embodiment, the mixed mode chromatographic support is ceramic hydroxyapatite. A buffer comprising about 5 mM sodium phosphate, pH 6.5, and about 0 M to about 1.5 M sodium chloride can be applied to the chromatographic support to elute the desired recombinant polypeptide. Alternatively, a buffer comprising about 5 mM to about 0.25 M sodium phosphate, pH 6.5, can be applied to the chromatographic support to elute the desired recombinant polypeptide In yet another embodiment, the hydrophobic interaction chromatographic support is polypropylene glycol (PPG) 600 M. A buffer comprising from about 0.7 M to 0 M sodium sulfate in about 20 mM sodium phosphate. pH 7.0 can be applied to the chromatographic support to elute the desired recombinant polypeptide.

Preferably, the eluate or fraction thereof from at least one of step (a), step (b) and step (c) is contacted with the lectin to detect the amount and/or type of glycosylated impurities in the eluate or fraction thereof. Different samples or eluates or fractions thereof containing the desired recombinant polypeptide can be pooled based on the amount and/or type of detected glycosylated impurity. For example, different samples or eluates or fractions thereof containing the desired recombinant polypeptide are pooled based on the amount and/or type of detected glycosylated impurity relative to the amount of recombinant polypeptide. In one embodiment, samples or eluate or fractions thereof comprising less than 10% glycovariant, less than 5% glycovariant, less than 1% glycovariant, or less than 0.5% glycovariant are pooled. Additionally, different samples or eluate or fractions thereof can be pooled based on the purity of the desired recombinant polypeptide. For example, samples or eluate or fractions thereof comprising greater than 91% purity, greater than 97% purity, or greater than 99% purity are pooled. In one embodiment, the purity is determined by measuring the mass of glycosylated heavy chain polypeptide and/or gly-cosylated light chain polypeptide as a percentage of total mass of heavy chain polypeptide and/or light chain poly-peptide. In a preferred embodiment, the eluate of step (c) comprises less than 50 ng/mg of glycovariant; more prefer-ably, the eluate of step (c) comprises less than 25 ng/mg of glycovariant; most preferably, the eluate of step (c) com-prises less than 10 ng/mg of glycovariant. In another pre-ferred embodiment, the eluate of step (c) comprises lectin activity ranging from about 0.2 to about 2 relative Units (RU) as measured by a lectin binding kinetic assay; more preferably, the eluate of step (c) comprises less than 10 ng/mg of fungal cell protein. In yet another preferred embodiment, the eluate of step (c) comprises less than 5 ng/mg of a fungal cell protein; more preferably, the eluate of step (c) comprises less than 2 ng/mg of a fungal cell protein. In yet a further preferred embodiment, the eluate of step (c) comprises less than 10 ng/mg of nucleic acid; more prefer-ably, the eluate of step (c) comprises less than 5 ng/mg of nucleic acid.

In another embodiment, certain samples or eluate or fractions thereof are discarded based on the amount and/or type of detected glycosylated impurities. In yet another embodiment, certain samples or fractions are treated to reduce and/or remove the glycosylated impurities based on the amount and/or type of detected glycosylated impurities. Exemplary treatments include one or more of the following: (i) addition of an enzyme or other chemical moiety that removes glycosylation. (ii) removal of the glycosylated impurities by effecting one or more lectin binding steps, (iii) effecting size exclusion chromatography to remove the glycosylated impurities.

In particular, the invention provides a process for purify-ing a desired recombinant polypeptide expressed in a fungal cell, preferably *Pichia pastoris*, from a mixture comprising the desired polypeptide and at least one glycosylated impu-rity, the purification process comprising: (a) contacting the mixture with an affinity chromatographic support and selec-tively eluting the multi-subunit protein from the support; (b) contacting the eluate or a fraction thereof of step (a) with a mixed mode chromatographic support and selectively elut-ing the multi-subunit protein from the support; and (c) contacting the eluate or a fraction thereof of step (b) with a hydrophobic interaction chromatographic support and selec-tively eluting the multi-subunit protein from the support, wherein the eluate or a fraction thereof of step (c) comprises substantially purified desired recombinant polypeptide. The amount and/or type of glycosylated impurities in the eluate or a fraction thereof of step (b) and/or step (c) is detected using a lectin that binds to said glycosylated impurities and one or more fractions of the eluate of step (b) and/or step (c) is selected for further processing based on the detected amount and/or type of glycosylated impurities. Preferably, the affinity chromatographic support is a Protein A column and/or the mixed mode chromatographic support is a hydroxyapatite column and/or the hydrophobic interaction chromatographic support is a PPG-600M column. Alterna-tively, the affinity chromatographic support is a lectin col-umn.

In one embodiment, the desired recombinant polypeptide is a multi-subunit protein, preferably an antibody. In another embodiment, the detection step is effected using at least one lectin selected from ConA, LCH, GNA, RCA, DC-SIGN, L-SIGN, PNA, AIL, VVL, WGA, SNA. MAL, MAH, UEA and AAL in a protein-protein interaction monitoring process selected from light interferometry (ForteBio Octet®), dual polarization interferometry (Farfield AnaLight®), static light scattering (Wyatt DynaPro NanoStar™), dynamic light scattering (Wyatt DynaPro NanoStar™), multi-angle light scattering (Wyatt Calypso II), surface plasmon resonance (ProteOn XPR36 or Biacore T100), ELISA, chemilumines-cent ELISA, far western, electrochemiluminescence (such as that done using a MesoScale Discovery) or other lectin kinetic binding assay. Preferably, the detection step is effected using GNA (or GNL) and/or DC-SIGN lectin(s) in a light interferometry (ForteBio Octet®) assay.

The invention further provides a fermentation process for producing a desired recombinant polypeptide and purifying the desired recombinant polypeptide from the fermentation medium. The process includes: (i) culturing a host cell or microbe under conditions that result in the expression and secretion of the recombinant polypeptide and one or more impurities into the fermentation medium; (ii) periodically obtaining one or more samples of the fermentation medium as the fermentation process proceeds or after different fer-mentation runs are conducted; (iii) detecting the amount and/or type of glycosylated impurities in the sample(s) using a lectin that binds to said glycosylated impurities, and (iv) based on the amount of detected glycosylated impurities in the sample(s) modifying one or more of the operating parameters or conditions of the fermentation process. The glycosylated impurity can be a glycovariant of the recom-binant polypeptide, preferably the result of O-linked glyco-sylation and/or N-linked glycosylation.

In one embodiment, the detection step is effected using at least one lectin, preferably a lectin bound to a support, selected from ConA, LCH, GNA, RCA, DC-SIGN, L-SIGN, PNA, AIL, VVL, WGA, SNA, MAL, MAH, UEA and AAL. In another embodiment, the detection step uses a protein-protein interaction monitoring process, such as light inter-ferometry (ForteBio Octet®), dual polarization interferom-etry (Farfield AnaLight®), static light scattering (Wyatt DynaPro NanoStar™), dynamic light scattering (Wyatt DynaPro NanoStar™), composition-gradient multi-angle light scattering (Wyatt Calypso II), surface plasmon reso-nance (ProteOn XPR36 or Biacore T100). ELISA, chemi-luminescent ELISA, far western, electrochemiluminescence (such as that done using a MesoScale Discovery) or other lectin kinetic binding assay.

In one embodiment, based on the amount of glycosylated impurities detected one or more of the following parameters or conditions of the fermentation process are altered: tem-perature, pH, gas constituent, feed constituent, agitation, aeration, antifoam and duration.

In another embodiment, the recombinant polypeptide is a homopolymeric or heteropolymeric polypeptide. Exemplary recombinant multimeric polypeptide include a hormone, growth factor, receptor, antibody, cytokine, receptor ligand, transcription factor or enzyme. Preferably, the recombinant polypeptide is an antibody or antibody fragment. Exemplary antibodies and antibody fragments include those that spe-cifically bind to IL-2, IL-4, IL-6, IL-10, IL-12, IL-13, IL-17, IL-18, IFN-alpha, IFN-gamma, BAFF, CXCL13, IP-10, CBP, angiotensin (angiotensin I and angiotensin II), Nav1.7, Nav1.8, VEGF, PDGF, EPO, EGF, FSH, TSH, hCG, CGRP. NGPF, TNF, HGF, BMP2, BMP7, PCSK9 or HRG. In one embodiment, the antibody or antibody fragment is a human antibody or a humanized antibody or fragment thereof. The humanized antibody can be of mouse, rat, rabbit, goat, sheep, or cow origin. Preferably, the humanized antibody is of rabbit origin. In one embodiment, the antibody or anti-body fragment comprises a monovalent bivalent, or multi-valent antibody.

In one embodiment, the host cell is a yeast or filamentous fungi. Preferably, the yeast host cell is selected from *Arxiozyma; Ascobolryozvma; Citeromyces; Debaryomytces; Dekkera; Eremothecium; Isatchenkia; Kazachstania; Kluwveromces; Kodamaea; Lodderomyces; Pachvsolen; Pichia; Saccharomyces; Saturnispora; Tetrapisispora; Torulaspora; Williopsis; Zygosaccharomyces; Yarrowia; Rhodosporidium; Candida; Hansenula; Filobasium; Sporidiobolus; Bullera; Leucosporidium* and *Filobasidella.* More preferably, the yeast host cell is *Pichia pastoris, Pichia angusta, Pichia guillermordii, Pichia nmetanolica,* or *Pichia inositovera.* Most preferably, the yeast host cell is *Pichia pastoria.* In a preferred embodiment, the *Pichia pastoris* expresses an antibody or antibody fragment. In an alternate embodiment, the filamentous fungal host cell is selected from *Aspergillus, Trichoderma, Penicillium, Rhizopus, Paecilomyces, Fusarium, Neurspora* and *Claviceps.*

In another embodiment, the process further includes recovering or purifying the recombinant polypeptide from the fermentation medium. Preferably, the purification process further comprises contacting the sample(s) with at least one chromatographic support and selectively eluting the desired recombinant polypeptide. In one embodiment, the purification process further comprises pooling different samples or eluates or fractions thereof containing the desired recombinant polypeptide based on the amount and/or type of detected glycosylated impurity. For example, different samples or eluates or fractions thereof containing the desired recombinant polypeptide can be pooled based on the amount and/or type of detected glycosylated impurity relative to the amount of recombinant polypeptide.

In one embodiment, the process further comprises detecting the amount of aggregated and/or disaggregated impurities in the samples or fractions using size exclusion chromatography. Preferably, based on the amount of aggregated and/or disaggregated impurities detected, one or more of the following parameters or conditions of the fermentation process are altered: temperature, pH, gas constituent, feed constituent, agitation, aeration, antifoam and duration.

BRIEF DESCRIPTION OF THE DRAWINGS

FIG. 1 provides an overview of an exemplary methodology for purification of monoclonal antibodies expressed in transformed cells, such as *Pichia,* from product-associated impurities, including monitoring the presence of impurities throughout the purification process.

FIG. 2 graphically illustrates lectin binding to a glycosylated protein. Lectin kinetic binding assays (such as light interferometry) are illustrated for use in an analytical technique to monitor the purification of a main product, e.g., antibody, from glycosylated impurities.

FIG. 3 graphically illustrates the presence of glycosylated variants, including O-linked glycosylated products, associated with the production of proteins in *Pichia.* Fractions from hydroxyapatite chromatographic separation of Ab-A were analyzed for the amount of glycosylated products present using an immobilized lectin (GNA. Snowdrop) in an Octet instrument.

FIG. 4A-B graphically illustrates that the level of glycosylated impurities determined by lectin kinetic binding assays correlate with the level of glycosylated impurities determined by size exclusion chromatography. The abbreviation GV refers to glycovariant. Lectin binding response data from Octet assays (RU) for GNA and DC-SIGN in hydroxyapatite chromatography fractions of Ab-A (Fraction 1-Fraction 21) are graphed with the percent glycovariant as determined by size exclusion (SE)-HPLC of the same fractions. See. FIG. 4A. A sample SE-HPLC chromatograph shows separation of glycovariant from IgG. The GV peak, which eluted at 15.9 minutes at room temperature) is marked with an arrow. The IgG peak eluted at 17.2 minutes at room temperature.

FIG. 5A-B shows the glycosylated impurity content of hydroxyapatite chromatography fractions of Ab-A produced in *Pichia,* which was used to determine which fractions to pool for further purification. For example, two pools were delineated based on different stringencies: Baseline Pooling Criteria—pool fractions with ≥91% purity and ≤5.0% variant (Fraction 1-Fraction 13); and Stringent Pooling Criteria—pool fractions with ≤1.0% variant (Fraction 1-Fraction 10). See, FIG. 5A. The abbreviation GV refers to glycovariant. SE-HPLC data shows that the Baseline Pool (Fraction 1-Fraction 13) has 0.4% GV, whereas the Stringent Pool (Fraction 1-Fraction 10) has 0.1% GV. O-glyco analysis (mol sugar/mol mAb) of the pools shows reduced monomannose and mannotriose in the Stringent Pool as compared to the Baseline Pool (i.e., 1.55 mol monomannose/mol Ab-A in the Stringent Pool compared to 1.60 mol monomannose/mol Ab-A in the Baseline Pool, and 0.22 mol mannotriose/mol Ab-A in the Stringent Pool compared to 0.28 mol mannotriose/mol Ab-A in the Baseline Pool). GNA-Octet response data (RU) confirmed reduced levels of glycovariants in the Stringent Criteria Pool compared to the Baseline Pool (i.e., 1.9 RU versus 2.3 RU, respectively). See, FIG. 5B.

FIG. 6A-B shows the glycosylated impurity content of hydrophobic interaction chromatography fractions of Ab-A produced in *Pichia,* which was used to determine which fractions to pool for further purification. For example, two possible pools were delineated based on different stringencies: Baseline Pooling Criteria—pool from first fraction with ≥97% purity on front flank to last fraction with ≥99% purity on rear flank (Fraction 4-Fraction 23); and Stringent Pooling Criteria—pool from first fraction with ≤10 RU GNA activity on front flank to last fraction with ≥99% SE-HPLC purity on rear flank (Fraction 8-Fraction 23). See, FIG. 6A. The abbreviation GV refers to glycovariant. The abbreviation LMW refers to low molecular weight impurities. SE-HPLC data shows that the Baseline Pool (Fraction 4-Fraction 23) has 0.4% GV, whereas the Stringent Pool (Fraction 8-Fraction 23) has 0.3% GV. O-glyco analysis (mol sugar/mol mAb) of the pools shows reduced monomannose, mannobiose and mannotriose in the Stringent Pool as compared to the Baseline Pool (i.e., 1.57 mol monomannose/mol Ab-A in the Stringent Pool compared to 1.48 mol monomannose/mol Ab-A in the Baseline Pool; 0.52 mol mannobiose/mol Ab-A in the Stringent Pool compared to 0.14 mol mannobiose mol/Ab-A mol in the Baseline Pool; and 0.32 mol mannotriose/mol Ab-A in the Stringent Pool compared to 0.07 mol mannotriose/mol Ab-A in the Baseline Pool). GNA-Octet data confirmed reduced levels of glycovariants in the Stringent Criteria Pool compared to the Baseline Pool (i.e., 1.1 RU versus 1.4 RU, respectively). See, FIG. 6B.

FIG. 8 shows a reduction in glycovariant (GV) impurities during downstream purification of Ab-B as monitored using the GNA lectin assay.

FIG. 9 shows a separation of glycovariant (GV) impurities during HIC purification of Ab-B. Pools of fractions from the HIC elution were tested for GV content using the GNA lectin assay. Fractions from the front of the elution peak (fraction 1-fraction 5) and fractions from the rear of the elution peak (fraction 26-fraction 32) has higher lectin activity than fractions from the middle of the peak (fraction 6-fraction 25). Also, fraction 6-fraction 25 contained the desired purified Ab-B product.

FIG. 10 shows stained SDS-PAGE gels run under non-reducing and reducing conditions (FIG. 10 panel A and panel B, respectively) of Ab-B produced in *Pichia*. Purification is observed as reduced levels of product-related impurities in processing from Protein A eluate to CHT pool to Phenyl HP HIC pool. In both panels: lanes 1, 2 and 6 contain molecular weight markers; lane 3 contains Protein A eluate; lane 4 contains CHT pool; and lane 5 contains HIC pool

DETAILED DESCRIPTION

Figure 4B:
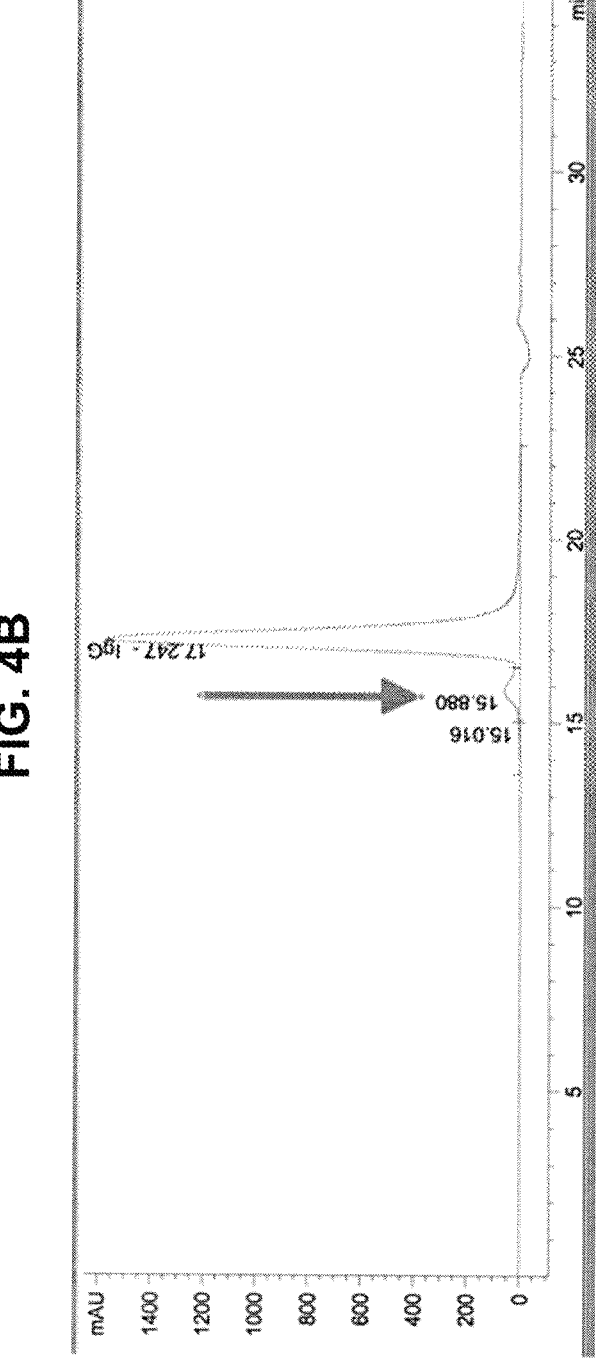

The present disclosure provides processes for producing and purifying recombinant polypeptides expressed by a host cell or microbe. In particular, the present disclosure provides processes of producing and purifying homopolymeric or heteropolymeric polypeptides, such an antibodies, expressed in yeast or filamentous fungal cells. The present methods incorporate lectin binding as a quantitative indicator of glycosylated impurities, such that the production and/or purification process can be modified to maximize the yield of the desired protein and decrease the presence of glycosylated impurities.

Additionally, the present processes encompass purification processes comprising chromatographic separation of samples from the fermentation process in order to substantially purify the desired recombinant polypeptide from undesired product-associated impurities, such as glycosylated impurities (e.g., glycovariants), nucleic acids and aggregates/disaggregates. In some embodiments, the eluate or fractions thereof from different chromatography steps are monitored for lectin binding activity to detect the type and/or amount of glycosylated impurities. Based on the amount and/or type of glycosylated impurities detected, certain samples from the fermentation process and/or fractions from the chromatographic purification are discarded, treated and/or selectively pooled for further purification.

In exemplary embodiments, the recombinant protein is an antibody or an antibody binding fragment, the yeast cell is *Pichia pastoris*, and the glycosylated impurity is a glycovariant of the desired recombinant polypeptide, such as an N-linked and/or O-linked glycovariant.

In a preferred embodiment, the recombinant protein is an antibody or antibody fragment, such as a humanized or human antibody, comprised of two heavy chain subunits and two light chain subunits. Preferred fungal cells include yeasts, and particularly preferred yeasts include methylotrophic yeast strains, e.g., *Pichia pastoris, Hansenula polymorpha (Pichia angusta), Pichia guillermordii, Pichia methanolica, Pichia inositovera*, and others (see. e.g., U.S. Pat. No. 4,812,405, 4,818,700, 4,929,555, 5,736,383, 5,955, 349, 5,888,768, and 6,258,559 each of which is incorporated by reference in its entirety). The yeast cell may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

Applicants have discovered novel processes for the production and purification of proteins produced in yeast or filamentous fungal cells that provides a high yield of the desired protein with minimal impurities. In particular, the processes disclosed herein incorporate purity monitoring steps into the protein production and/or purification schemes to improve the removal of product-associated impurities, e.g., glycosylated impurities, from the main protein product of interest, e.g., by selectively discarding, treating and/or purifying certain fractions from the production and/or purification schemes based on the amount and/or type of detected glycosylated impurity relative to the amount of recombinant polypeptide. The working examples demonstrate that employing such production and purification monitoring methods results in high levels of product purification (e.g., at least 97% purity) while maintaining a high yield of the desired protein product.

In one embodiment, the methods include a fermentation process for producing a desired recombinant polypeptide and purifying the desired recombinant polypeptide from the fermentation medium. Generally, a yeast cell or microbe is cultured under conditions resulting in expression and secretion of the recombinant polypeptide as well as one or more impurities into the fermentation medium, a sample is collected, e.g., during or after the fermentation run, and the amount and/or type of glycosylated impurities in the sample(s) is monitored using a lectin, such that parameters of the fermentation process, e.g., temperature, pH, gas constituents (e.g., oxygen level, pressure, flow rate), feed constituents (e.g., glucose level or rate), agitation, aeration, antifoam (e.g., type or concentration) and duration, can be modified based on the detected glycosylated impurities.

In another embodiment, the methods include a process for purifying a desired recombinant polypeptide from one or more samples, which result from a fermentation process that comprises culturing a desired cell or microbe under conditions that result in the expression and secretion of the recombinant polypeptide and one or more impurities into the fermentation medium, by using lectin binding to detect the amount and/or type of glycosylated impurities in the sample(s). The inventors have determined that lectin kinetic binding assays provide a quantitative measure of glycosylated impurities, such that the purification process can be adjusted in response to the detected level and type of impurity.

In a particular embodiment, the purification process further includes contacting one or more samples from the fermentation process, e.g., fermentation medium containing the desired recombinant protein, e.g., an antibody, expressed in a host yeast or filamentous fungal cell and an impurity, with at least one chromatographic support and then selectively eluting the desired recombinant polypeptide. For example, the fermentation process sample may be tested for the glycosylated impurities using a kinetic lectin binding assay and, depending on the type and/or amount of glycosylated impurities detected, contacted with an affinity chromatographic support (e.g., Protein A or lectin), a mixed mode chromatographic support (e.g., ceramic hydroxyapatite) and a hydrophobic interaction chromatographic support (e.g., polypropylene glycol (PPG) 600M). The desired protein is separated, e.g., selectively eluted, from each chromatographic support prior to being contacted with the subsequent chromatographic support, resulting in the eluate or a fraction thereof from hydrophobic interaction chromatographic support comprising a substantially purified desired recombinant protein.

"Substantially purified" with regard to the desired protein or multi-subunit protein means that the sample comprises at least 90%, at least 91%, at least 92%, at least 93%, at least 94%, at least 95%, at least 96%, at least 97%, at least 98%, or at least 98.5% of the desired recombinant protein with less than 3%, less than 2.5%, less than 2%, less than 1.5% or less than 1% of impurities. i.e., aggregate, variant and low molecular weight product. In one embodiment, the substantially purified protein comprises less than 50 ng/mg, preferably less than 25 ng/mg or more preferably less than 10 ng/mg of glycovariant; less than 10 ng/mg, preferably less than 5 ng/mg or more preferably less than 2 ng/mg of fungal cell protein; and/or less than 10 ng/mg or preferably less than 5 ng/mg of nucleic acid.

The methods optionally further include monitoring a sample of the fermentation process and/or a portion of the eluate or a fraction thereof from at least one of the affinity chromatographic support, the mixed mode chromatographic support and the hydrophobic interaction chromatographic support for the presence of at least one product-associated impurity, such as a fungal cell protein, a fungal cell nucleic acid, an adventitious virus, an endogenous virus, an endotoxin, an aggregate, a disaggregate, or an undesired protein comprising at least one modification relative to the desired recombinant protein (e.g., an amino acid substitution, N-terminal modification, C-terminal modification, mismatched S—S bonds, folding, truncation, aggregation, multimer dissociation, denaturation, acetylation, fatty acylation, deamidation, oxidation, carbamylation, carboxylation, formylation, gamma-carboxyglutamylation, glycosylation, methylation, phosphorylation, sulphation, PEGylation and ubiquitination). In particular, the production and purification processes may include detecting the amount of aggregated and/or disaggregated impurities in the samples or fractions using size exclusion chromatography.

Though much of the present disclosure describes production of antibodies, the methods described herein are readily adapted to other multi-subunit complexes as well as single subunit proteins. The methods disclosed herein may readily be utilized to improve the yield and/or purity of any recombinant multi-subunit complex comprising two or more different subunits. Additionally, the present methods are not limited to production of multi-protein complexes but may also be readily adapted for use with ribonucleoprotein (RNP) complexes including telomerase, hnRNPs, ribosomes, snRNPs, signal recognition particles, prokaryotic and eukaryotic RNase P complexes, and any other complexes that contain multiple distinct protein and/or RNA subunits. The fungal cell that expresses the multi-subunit complex may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

Expression of Recombinant Proteins

Recombinant proteins, including homopolymeric or heteropolymeric polypeptides, e.g., an antibody or an antibody fragment, can be expressed in yeast and filamentous fungal cells. In one embodiment, the desired protein is recombinantly expressed in yeast, and particularly preferred yeasts include methylotrophic yeast strains. e.g., *Pichia pastoris.*

*Hansenula polyrmorpha (Pichia angusta), Pichia guillermordii, Pichia methanolica, Pichia inositovera,* and others (see, e.g., U.S. Pat. Nos. 4,812,405, 4,818,700, 4,929,555, 5,736,383, 5,955,349, 5,888,768, and 6,258,559 each of which is incorporated by reference in its entirety). Other exemplary yeast include *Arxiozyma; Ascobotlrvzvma; Citeronyces; Debaryomyces; Dekkera; Eremothecium; Issatchenkia; Kazachsania; Kluyveromyces; Kodamaea; Lodderomyces; Pachysolen; Pichia; Saccharomyces; Saturnispora; Tetrapisispora; Torulaspora; Williopsis; Zygosaccharomyes; Yarrowia; Rhodsporidium; Candida; Hansenula; Filobasium; Sporidiobolus; Bullera; Leucosporidium* and *Filobasidella.*

The yeast cell may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

In one embodiment, the yeast cell may comprise more than one copy of one or more of the genes encoding the recombinant protein or subunits of the desired multi-subunit protein. For example, multiple copies of a subunit gene may be integrated in tandem into one or more chromosomal loci. Tandemly integrated gene copies are preferably retained in a stable number of copies during culture for the production of the desired protein or multi-subunit complex. For example, in prior work described by the present applicants, gene copy numbers were generally stable for *P. pastoris* strains containing three to four tandemly integrated copies of light and heavy chain antibody genes (see. U.S. 20130045888).

One or more of the genes encoding the recombinant protein subunits are preferably integrated into one or more chromosomal loci of a fungal cell. Any suitable chromosomal locus may be utilized for integration, including intergenic sequences, promoters sequences, coding sequences, termination sequences, regulatory sequences, etc. Exemplary chromosomal loci that may be used in *P. pastoris* include PpURA5; OCH1; AOX1; HIS4; and GAP. The encoding genes may also be integrated into one or more random chromosomal loci rather than being targeted. In preferred embodiments, the chromosomal loci are selected from the group consisting of the pGAP locus, the 3'AOX TT locus and the HIS4 TT locus. In additional exemplary embodiments, the genes encoding the heterologous protein subunits may be contained in one or more extrachromosomal elements, for example one or more plasmids or artificial chromosomes.

In exemplary embodiments, the protein may be a multi-subunit protein that, e.g., comprises two, three, four, five, six, or more identical and/or non-identical subunits. Additionally, each subunit may be present one or more times in each multi-subunit protein. For example, the multi-subunit protein may be a multi-specific antibody such as a bi-specific antibody comprising two non-identical light chains and two non-identical heavy chains. A panel of diploid or tetraploid yeast cells containing differing combinations of gene copy numbers may be quickly generated by mating cells containing varying copy numbers of the individual subunit genes. Antibody production from each strain in the panel may then be assessed to identify a strain for further use based on a characteristic such as yield of the desired multi-subunit protein or purity of the desired multi-subunit protein relative to undesired side-products.

The subunits of a multi-subunit may be expressed from monocistronic genes, polycistronic genes, or any combination thereof. Each polycistronic gene may comprise multiple copies of the same subunit, or may comprise one or more copies of each different subunit.

Exemplary methods that may be used for manipulation of Pichiapatoris (including methods of culturing, transforming, and mating) are disclosed in Published Applications including U.S. 20080003643, U.S. 20070298500, and U.S. 20060270045, and in Higgins, D. R., and Cregg, J. M., Eds. 1998. *Pichia* Protocols. Methods in Molecular Biology. Humana Press, Totowa, N.J., and Cregg, J. M., Ed., 2007, *Pichia* Protocols (2nd edition), Methods in Molecular Biology. Humana Press, Totowa, N.J., each of which is incorporated by reference in its entirety.

An exemplary expression cassette that may be utilized is composed of the glyceraldehyde dehydrogenase gene (GAP gene) promoter, fused to sequences encoding a secretion signal, followed by the sequence of the gene to be expressed, followed by sequences encoding a *P. pastoris* transcriptional termination signal from the *P. pastoris* alcohol oxidase I gene (AOX1). The Zeocin resistance marker gene may provide a means of enrichment for strains that contain multiple integrated copies of an expression vector in a strain by selecting for transformants that are resistant to higher levels of Zeocin. Similarly, G418 or Kanamycin resistance marker genes may be used to provide a means of enrichment for strains that contain multiple integrated copies of an expression vector in a strain by selecting for transformants that are resistant to higher levels of Geneticin or Kanamycin.

Yeast strains that may be utilized include auxotrophic *P. pastoris* or other *Pichia* strains, for example, strains having mutations in met1, lys3, ura3 and ade1 or other auxotrophy-associated genes. Preferred mutations are incapable of giving rise to revertants at any appreciable frequency and are preferably partial or even more preferably full deletion mutants. Preferably, prototrophic diploid or tetraploid strains are produced by mating a complementing sets of auxotrophic strains.

Prior to transformation, each expression vector may be linearized by restriction enzyme cleavage within a region homologous to the target genomic locus (e.g., the GAP promoter sequence) to direct the integration of the vectors into the target locus in the fungal cell. Samples of each vector may then be individually transformed into cultures of the desired strains by electroporation or other methods, and successful transformants may be selected by means of a selectable marker, e.g., antibiotic resistance or complementation of an auxotrophy. Isolates may be picked, streaked for single colonies under selective conditions and then examined to confirm the number of copies of the gene encoding the desired protein or subunit of the multi-subunit complex (e.g., a desired antibody) by Southern Blot or PCR assay on genomic DNA extracted from each strain. Optionally, expression of the expected subunit gene product may be confirmed, e.g., by FACS, Western Blot, colony lift and immunoblot, and other means known in the art. Optionally, haploid isolates are transformed additional times to introduce additional heterologous genes, e.g., additional copies of the same subunit integrated at a different locus, and/or copies of a different subunit. The haploid strains are then mated to generate diploid strains (or strains of higher ploidy) able to synthesize the multi-protein complex. Presence of each expected subunit gene may be confirmed by Southern blotting, PCR, and other detection means known in the art. Where the desired multi-protein complex is an antibody, its expression may also be confirmed by a colony lift/immunoblot method (Wung et al. Biotechniques 21 808-812 (1996)) and/or by FACS.

This transformation protocol is optionally repeated to target a heterologous gene into a second locus, which may be the same gene or a different gene than was targeted into the first locus. When the construct to be integrated into the second locus encodes a protein that is the same as or highly similar to the sequence encoded by the first locus, its sequence may be varied to decrease the likelihood of undesired integration into the first locus. For example, the sequence to be integrated into the second locus may have differences in the promoter sequence, termination sequence, codon usage, and/or other tolerable sequence differences relative to the sequence integrated into the first locus.

Transformation of haploid *P. pastoris* strains and genetic manipulation of the *P. pastoris* sexual cycle may be performed as described in *Pichia* Protocols (1998, 2007), supra.

Expression vectors for use in the methods of the invention may further include yeast specific sequences, including a selectable auxotrophic or drug marker for identifying transformed yeast strains. A drug marker may further be used to amplify copy number of the vector in a yeast cell, e.g., by culturing a population of cells in an elevated concentration of the drug, thereby selecting transformants that express elevated levels of the resistance gene.

The polypeptide coding sequence of interest is typically operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included. e.g. a signal sequence, and the like. A yeast origin of replication is optional, as expression vectors are often integrated into the yeast genome.

In an exemplary embodiment, one or more of the genes encoding the heterologous protein or subunits thereof are coupled to an inducible promoter. Suitable exemplary promoters include the alcohol oxidase 1 gene promoter, formaldehyde dehydrogenase genes (FLD; see U.S. Pub. No. 2007/0298500), and other inducible promoters known in the art. The alcohol oxidase 1 gene promoter, is tightly repressed during growth of the yeast on most common carbon sources, such as glucose, glycerol, or ethanol, but is highly induced during growth on methanol (Tschopp et al., 1987; U.S. Pat. No. 4,855,231 to Stroman, D. W., et al). For production of foreign proteins, strains may be initially grown on a repressing carbon source to generate biomass and then shifted to methanol as the sole (or main) carbon and energy source to induce expression of the foreign gene. One advantage of this regulatory system is that *P. pastoris* strains transformed with foreign genes whose expression products are toxic to the cells can be maintained by growing under repressing conditions.

In another exemplary embodiment, one or more of the heterologous genes may be coupled to a regulated promoter, whose expression level can be upregulated under appropriate conditions. Examples of suitable promoters from *Pichia* include the CUP1 (induced by the level of copper in the medium), tetracycline inducible promoters, thiamine inducible promoters. AOX1 promoter (Cregg et al. (1989) Mol. Cell. Biol. 9:1316-1323); ICL1 promoter (Menendez et al. (2003) Yeast 20(13); 1097-108); glyceraldehyde-3-phosphate dehydrogenase promoter (GAP) (Waterham et al. (1997) Gene 186(1):37-44); and FLD1 promoter (Shen et al. (1998) Gene 216(i); 93-102). The GAP promoter is a strong constitutive promoter and the CUP1, AOX and FLD1 promoters are inducible. Each foregoing reference is incorporated by reference herein in its entirety.

Other yeast promoters include ADHt, alcohol dehydrogenase II, GAL4, PHO3. PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide. e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the fungal cell. The S. cerevisiae alpha factor pre-pro signal has proven effective in the secretion of a variety of recombinant proteins from P. pastoris. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence. PHA-E, FACE, human MCP-I human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998), each of which is incorporated by reference herein in its entirety.

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Though optional, in one embodiment, one or more subunit of the desired protein or multi-subunit complex is operably linked, or fused, to a secretion sequence that provides for secretion of the expressed polypeptide into the culture media, which can ticilitate harvesting and purification of the heterologous protein or multi-subunit complex. Even more preferably, the secretion sequences provide for optimized secretion of the polypeptide from the fungal cells (e.g., yeast diploid cells), such as through selecting preferred codons and/or altering the percentage of AT base pairs through codon selection. It is known in the art that secretion efficiency and/or stability can be affected by the choice of secretion sequence and the optimal secretion sequence can vary between different proteins (see. e.g., Koganesawa et al. Protein Eng. 2001 September; 14(9):705-10, which is incorporated by reference herein in its entirety). Many potentially suitable secretion signals are known in the art and can readily be tested for their effect upon yield and/or purity of a particular heterologous protein or multi-subunit complex. Any secretion sequences may potentially be used, including those present in secreted proteins of yeasts and other species, as well as engineered secretion sequences. See Hashimoto et al., Protein Engineering vol. 11 no. 2 pp. 75-77, 1998; Oka et al., Biosci Biotechnol Biochem. 1999 November; 63(11): 1977-83; Gellissen et al., FEMS Yeast Research 5 (2005) 1079-1096; Ma et al., Hepatology. 2005 December; 42(6): 1355-63; Raemackers et al., Eur J Biochem. 1999 Oct. 1; 265(1): 394-403; Koganesawa ct al., Protein Eng. (2001) 14 (9): 705-710; Daly et al., Protein Expr Purif. 2006 April; 46(2):456-67; Damasceno et al., Appi Microbiol Iiotechnol (2007) 74:381-389; and Felgenhauer et al., Nucleic Acids Res. 1990 Aug. 25:18(16):4927, each of which is incorporated by reference herein in its entirety).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking may be accomplished by ligation at convenient restriction sites or alternatively via a PCR/recombination method familiar to those skilled in the art (Gateway4 Technology: Invitrogen, Carlsbad Calif.). If such sites do not exist, the synthetic oligonuclcotide adapters or linkers may be used in accordance with conventional practice. Desired nucleic acids (including nucleic acids comprising operably linked sequences) may also be produced by chemical synthesis.

The protein may also be secreted into the culture media without being operably linked or fused to a secretion signal. For example, it has been demonstrated that some heterologous polypeptides are secreted into the culture media when expressed in P. pastoris even without being linked or fused to a secretion signal. Additionally, the protein may be purified from fungal cells (which, for example, may be preferable if the protein is poorly secreted) using methods known in the art.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

As used herein the terms "filamentous fungal cell" and "filamentous fungal host cell" are used interchangeably and are intended to mean any cell from any species from the genera *Aspergillus, Trichderma, Penicillium, Rhiropus,*

*Paecilonmyces, Fusarium, Neurospora* and *Claviceps*. In the present invention this is intended to broadly encompass any filamentous fungal cell that can be grown in culture.

As used herein the term "yeast cell" refers to any cell from any species from the genera *Arxiozyma; Ascobotrozyma; Citerornyces; Debaryomyces; Dekkera; Eremothecium; Issatchenkia; Kazachstania; Kluyveronmvces; Kodamaea; Lodderomyces; Pachysolen; Pichia; Saccharromyces; Saturnispora; Teirapiispora; Torulaspora; Williopsis; Zygosaccharomyces; Yarrowia, Rhodosporidium; Candida; Hansenulda; Filobasium; Sporidiobolus; Bullera; Leucosporidium* and *Filobasidella*. In the present invention, this is intended to broadly encompass any yeast cell that can be grown in culture.

In a preferred embodiment of the invention, the yeast cell is a member of the genus *Pichia* or is another methylotroph. In a further preferred embodiment of the invention, the fungal cell is of the genus *Pichia* is one of the following species: *Pichia pastoris, Pichia methanalica*, and *Hansenula polymorpha (Pichia angusta)*. In a particularly preferred embodiment of the invention, the fungal cell of the genus *Pichia* is the species *Pichia pastoris*.

Such species may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or fusion (e.g., spheroplast fusion).

As used herein "haploid yeast cell" refers to a cell having a single copy of each gene of its normal genomic (chromosomal) complement.

As used herein, "polyploid yeast cell" refers to a cell having more than one copy of its normal genomic (chromosomal) complement.

As used herein. "diploid yeast cell" refers to a cell having two copies (alleles) of essentially every gene of its normal genomic complement, typically formed by the process of fusion (mating) of two haploid cells.

As used herein, "tetraploid yeast cell" refers to a cell having four copies (alleles) of essentially every gene of its normal genomic complement, typically formed by the process of fusion (mating) of two diploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]: and a [met arg] haploid can be mated with [ade arg] haploid to obtain diploid [arg]; then the diploid [his] can be mated with the diploid [arg] to obtain a tetraploid prototroph. It will be understood by those of skill in the art that reference to the benefits and uses of diploid cells may also apply to tetraploid cells.

As used herein, "yeast mating" refers to the process by which two yeast cells fuse to form a single yeast cell. The fused cells may be haploid cells or cells of higher ploidy (e.g., mating two diploid cells to produce a tetraploid cell).

As used herein. "meiosis" refers to the process by which a diploid yeast cell undergoes reductive division to form four haploid spore products. Each spore may then germinate and form a haploid vegetatively growing cell line.

As used herein, "folding" refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic Protein Disulfide Isomerase (PDI) is not only an efficient catalyst of protein cysteine oxidation and disulfide bond isomerization, but also exhibits chaperone activity. Co-expression of PDI can facilitate the production of active proteins having multiple disultide bonds. Also of interest is the expression of BIP (immunoglobulin heavy chain binding protein); cyclophilin; and the like. In one embodiment of the invention, the desired protein or multi-subunit complex may be expressed from a yeast strain produced by mating, wherein each of the haploid parental strains expresses a distinct folding enzyme, e.g. one strain may express BIP, and the other strain may express PDI or combinations thereof.

The terms "desired protein" and "desired recombinant protein" are used interchangeably and refer generally to a heterologous protein expressed in a host yeast or filamentous fungal cell comprising a particular primary, secondary, tertiary and/or quaternary structure with a particular pattern of post-translational and/or other modifications. In one aspect, the desired protein is a homopolymeric or heteropolymeric multi-subunit protein. Exemplary multimeric recombinant proteins include, but are not limited to, a multimeric hormone (e.g., insulin family, relaxin family and other peptide hormones), growth factor, receptor, antibody, cytokine, receptor ligand, transcription factor or enzyme.

Preferably, the desired recombinant protein is an antibody or an antibody fragment, such as a humanized or human antibody or a binding portion thereof. In one aspect, the humanized antibody is of mouse, rat, rabbit, goat, sheep, or cow origin. Preferably, the humanized antibody is of rabbit origin. In another aspect, the antibody or antibody fragment comprises a monovalent, bivalent, or multivalent antibody. In yet another aspect, the antibody or antibody fragment specifically binds to IL-2, IL-4, IL-6, IL-10, IL-12, IL-13, IL-17, IL-18, IFN-alpha, IFN-gamma. BAFF, CXCL13, IP-10, CBP, angiotensin (angiotensin I and angiotensin II). Nav1.7. Nav1.8, VEGF, PDGF, EPO, EGF, FSH, TSH, hCG, CGRP, NGF, TNF, HGF, BMP2, BMP7, PCSK9 or HRG.

The term "antibody" includes any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, human antibodies, single chain antibodies such as scFvs, camelbodies, nanobodies. IgNAR (single-chain antibodies derived from sharks), small-modular immunopharmaceuticals (SMIPs), and antibody fragments such as Fabs. Fab'. F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al. A new antigen receptor gene family that undergoes rearrangement and extensive somatic diversification in sharks, Nature. 1995 Mar. 9; 374(6518): 168-73; Nuttall S D, et al., Isolation of the new antigen receptor from wobbegong sharks, and use as a scaffold for the display of protein loop libraries. Mol Immunol. 2001 August: 38(4):313-26; H-lamers-Casterman C, et al., Naturally occurring antibodies devoid of light chains, Nature. 1993 Jun. 3: 363(6428):446-8; Gill D S, et al., Biopharmaceutical drug discovery using novel protein scaffolds, Curr Opin Biotechnol. 2006 December; 17(6):653-8. Epub 2006 Oct. 19. Each foregoing reference is incorporated by reference herein in its entirety.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions (V$_L$ and V$_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3 or IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference. Methods of humanizing antibodies have been described previously in issued U.S. Pat. No. 7,935,340, the disclosure of which is incorporated herein by reference in its entirety. In some instances, a determination of whether additional rabbit framework residues are required to maintain activity is necessary. In some instances the humanized antibodies still requires some critical rabbit framework residues to be retained to minimize loss of affinity or activity. In these cases, it is necessary to change single or multiple framework amino acids from human germline sequences back to the original rabbit amino acids in order to have desired activity. These changes are determined experimentally to identify which rabbit residues are necessary to preserve affinity and activity.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest. e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

As used herein, "half antibody". "half-antibody species" or "HIL1" refer to a protein complex that includes a single heavy and single light antibody chain, but lacks a covalent linkage to a second heavy and light antibody chain. Two half antibodies may remain non-covalently associated under some conditions (which may give behavior similar to a full antibody. e.g., apparent molecular weight determined by size exclusion chromatography). Similarly, H2L1 refers to a protein complex that includes two heavy antibody chains and single light antibody chain, but lacks a covalent linkage to a second light antibody chain; these complexes may also non-covalently associate with another light antibody chain (and likewise give similar behavior to a full antibody). Like full antibodies, half antibody species and H2L1 species can dissociate under reducing conditions into individual heavy and light chains. Half antibody species and H2L1 species can be detected on a non-reduced SDS-PAGE gel as a species migrating at a lower apparent molecular weight than the full antibody, e.g., H1L1 migrates at approximately half the apparent molecular weight of the full antibody (e.g., about 75 kDa).

As used herein, "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 50-500 mg/liter (after about 90 hours in culture) and preferably substantially greater.

As used herein, "polyploidal yeast culture that secretes desired amounts of recombinant polypeptide" refers to cultures that stably or for prolonged periods secrete at least at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription ofmRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in the following review articles, each of which is incorporated by reference herein in its entirety: Van Brunt 1990. Bio/Technol., 8(4):291-294: and Gill and Ghaemi, Nucleosides Nucleotides Nucleic Acids. 2008 March; 27(3):224-43. Polymerase chain reaction or PCR is a prototype of nucleic acid amplification, and use of PCR herein should be considered exemplary of other suitable amplification techniques.

The general structure of antibodies in most vertebrates (including mammals) is now well understood (Edelman. G. M., Ann. N.Y. Acad. Sci., 190: 5 (1971)). Conventional antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_b$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to gamma, mu, alpha, delta, and epsilon heavy chain constant regions). The constant region or class determines subsequent effector function of the antibody, including activation of complement (Kabat. E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)): while the variable region determines the antigen with which it will react. Light chains are classified as either kappa or lambda. Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_L$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri. S., Methods. 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

The expression "stable copy number" refers to a host cell that substantially maintains the number of copies of a gene (such as an antibody chain gene) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, at least 50%, and preferably at least 70%. 75%, 85%, 90%, 95%, or more of cells in the culture may maintain the same number of copies of the gene as in the starting cell. In a preferred embodiment, the host cell contains a stable copy number of the gene encoding the desired protein or encoding each subunit of the desired multi-subunit complex (e.g., antibody).

The expression "stably expresses" refers to a host cell that maintains similar levels of expression of a gene or protein (such as an antibody) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, the rate of production or yield of the gene or protein may be at least 50%, and preferably at least 70%, 75%, 85%, 90%, 95%, or more of the initial rate of production. In a preferred embodiment, the host cell stably expresses the desired protein or multi-subunit complex (e.g., antibody).

Recovery and Purification of Recombinant Proteins

Monoclonal antibodies have become prominent therapeutic agents, but their purification process needs to reliably and predictably produce a product suitable for use in humans. Impurities such as host cell protein, DNA, adventitious and endogenous viruses, endotoxin, aggregates and other species. e.g., glycovariants, must be controlled while maintaining an acceptable yield of the desired antibody product. In addition, impurities introduced during the purification process (e.g., leached Protein A, extractables from resins and filters, process buffers and agents such as detergents) must be removed as well before the antibody can be used as a therapeutic agent.

Primary Recovery Processes

The first step in the recovery of an antibody from cell culture is harvest. Cells and cell debris are removed to yield a clarified, filtered fluid suitable for chromatography. i.e., harvested cell culture fluid (HCCF). Exemplary methods for primary recovery include centrifugation, depth filtration and sterile filtration, flocculation, precipitation and/or other applicable approaches depending on scale and facility capability.

Centrifugation

In one embodiment, cells and flocculated debris are removed from broth by centrifugation. Centrifugation can be used for pilot and commercial scale manufacturing. Preferably, centrifugation is used in large scale manufacturing to provide harvested cell culture fluid from cell cultures with percent solids of >3% (i.e., increased levels of sub-micron debris).

Standard non-hermetic disc-stack centrifuges as well fully hermetic centrifuges as are capable of removing cells and large cell debris, although fully hermetic centrifuges can significantly reduce the amount of cell lysis that is incurred during this unit operation, e.g., by at least 50%, by preventing overflow and minimizing shear.

The clarification efficiency of the centrifugation process is affected by harvest parameters such as centrifuge feed rate. G-force, bowl geometry, operating pressures, discharge frequency and ancillary equipment used in the transfer of cell culture fluid to the centrifuge. The cell culture process characteristics such as peak cell density, total cell density and culture viability during the culture process and at harvest can also affect separation performance. The centrifugation process can be optimized to select the feed rate and bowl rotational speed using the scaling factors of feed rate (Q) and equivalent settling area ($\Sigma$) in the centrifuge. The optimized process can minimize cell lysis and debris generation while maximizing the sedimentation of submicron particles and product yield.

Filtration

Tangential flow microfiltration can also be used in cell harvest. In particular, the cell culture fluid flows tangential to the microporous membrane, and pressure driven filtrate flow separates the soluble product from the larger, insoluble cells. Membrane fouling is limited by the inertial lift and shear-induced diffusion generated by the turbulent flow across the membrane surface.

A high yielding harvest can be achieved by a series of concentration and diafiltration steps. In the former, the volume of the cell culture fluid is reduced, which results in concentrating the solid mass. The diafiltration step then washes the product from the concentrated cell culture fluid mixture.

By way of example, a 0.22 μm pore size may be employed for the TFF membrane as it produces the target quality harvested cell culture fluid (suitable for chromatography) without the need for further clarification. Alternatively, more open pore sizes at the TFF barrier may be used to better manage fouling; however, more open pore sizes may require an additional clarification step (e.g., normal flow depth filtration) downstream of the TFF system. Preferably, TFF is used for cell cultures with percent solids of <3%.

Depth filters can also be used in the clarification of cell culture broths, to maintain capacity on membrane filters or to protect chromatography columns or virus filters. Depth filters may be composed of, e.g., cellulose, a porous filter-aid such as diatomaceous earth, an ionic charged resin binder and a binding resin (present at a small weight percent to covalently bind dissimilar construction materials together, giving the resultant media wet strength and conferring positive charge to the media surfaces). Depth filters rely on both size exclusion and adsorptive binding to effect separation. Exemplary depth filters are approximately 2-4 mm thick.

For harvesting applications, depth filters can be applied directly with the whole cell broth or in conjunction with a primary separator, e.g., TFF or centrifugation. For example, when used for whole-cell broth depth filter harvest, the filtration train contains three stages of filters: (1) the primary stage with a coarse or open depth filter with a pore size of up to 10 μm to remove whole cells and large particles; (2) the secondary stage with a tighter depth filter to clear colloidal and submicron particles; and (3) the third stage with a 0.2 μm pore size membrane filter. Although the filtration process generally scales linearly, a safety factor of 1.5× to >3× can be employed for each stage to ensure adequate filter capacity.

In one embodiment, a depth filter is employed after centrifugation to further clarify the harvested broth, e.g., because there is a practical lower limit to the particle size that can be removed by centrifugation. For example, the depth filter may comprise two distinct layers (with the upstream zone being a coarser grade compared with the downstream) and have a pore size range of 0.1-4 μm. The larger particles are trapped in the coarse grade filter media and smaller particles are trapped in the tighter media, reducing premature plugging and increasing filtration capacity.

Optimization of filter type, pore size, surface area and flux can be done at lab bench scale and then scaled up to pilot scale based on, e.g., the centrate turbidity and particle size distribution. Depth filter sizing experiments are generally performed at constant flux using pressure endpoints in any one or combination of filtration stages. Preferably, a 0.22 μm grade filter is used to filter the supernatant at the end of harvest process to control bioburden. The 0.22 μm-filtered supernatant can be stored at 2-8° C. for several days or longer without changing the antibody product-related variant profile.

Without being bound by theory, it is believed that the adsorptive mechanism of depth filters allows for their extensive use as a purification tool to remove a wide range of process contaminants and impurities. In particular, the electrostatic interactions between the positive charges of depth filters and DNA molecules as well as hydrophobic interactions between depth filter media and DNA molecules may play important roles in the adsorptive reduction of DNA. For example, charged depth filters have been used to remove DNA, and the level of charges on Zeta Plus (Cuno) 90SP has been correlated with its ability to remove DNA. Additionally, by way of example, positively charged depth filters have been used to remove *Escherichia coli*-derived and other endogenous endotoxins and viruses many times smaller than the average pore size of the filter, and Zeta Plus® (Cuno) VR series depth filters were found to bind enveloped retrovirus and non-enveloped parvovirus by adsorption. Depth filtration was also employed to remove spiked prions from an immunoglobin solution. Moreover, the removal of host cell proteins through depth filtration prior to a Protein A affinity chromatography column has been shown to significantly reduce precipitation during the pH adjustment of the Protein A pool.

Flocculation and Precipitation

In one embodiment, precipitation/flocculation-based pretreatment steps are used to reduce the quantity of cell debris and colloids in the cell culture fluid, which can exceed the existing filtration train equipment capability. Flocculation involves polymer adsorption, e.g., electrostatic attraction, to the cell and cell debris by, e.g., cationic, neutral and anionic polymers, to clear cellular contaminants resulting in improved clarification efficiency and high recovery yield. Flocculation reagents. e.g., calcium chloride and potassium phosphate, at very low levels. e.g., 20-60 mM calcium chloride with an equimolar amount of phosphate added to form calcium phosphate, are believed to contribute to co-precipitation of calcium phosphate with cells, cell debris and impurities.

In one embodiment, the disclosed purification processes include treatment of the whole cell broth with ethylene diamine tetraacetic acid (EDTA) to 3 mM final concentration and with a flocculating agent, subsequent removal of cells and flocculated debris by centrifugation, followed by clarification through depth and 0.2 μm filters.

Chromatography

In the biopharmaceutical industry, chromatography is a critical and widely used separation and purification technology due to its high resolution. Chromatography exploits the physical and chemical differences between biomolecules for separation. For example, protein A chromatography may follow harvest to yield a relatively pure product that requires removal of only a small proportion of process and product related impurities. One or two additional chromatography steps can then be employed as polishing steps, e.g., incorporating ion exchange chromatography, hydrophobic interaction chromatography, mixed mode chromatography and/or hydroxyapatite chromatography. These steps can provide additional viral, host cell protein and DNA clearance, as well as removing aggregates, unwanted product variant species and other minor contaminants. Lastly, the purified product may be concentrated and diafiltered into the final formulation buffer.

Antibody purification involves selective enrichment or specific isolation of antibodies from serum (polyclonal antibodies), ascites fluid or cell culture supernatant of a cell line (monoclonal antibodies). Purification methods range from very crude to highly specific and can be classified as follows:

Physicochemical fractionation—differential precipitation, size-exclusion or solid-phase binding of immunoglobulins based on size, charge or other shared chemical characteristics of antibodies in typical samples. This isolates a subset of sample proteins that includes the immunoglobulins.

Affinity fractionation—binding of particular antibody classes (e.g., IgG) by immobilized biological ligands (e.g., proteins) that have specific affinity to immunoglobulins (which purifies all antibodies of the target class without regard to antigen specificity) or affinity purification of only those antibodies in a sample that bind to a particular antigen molecule through their specific antigen-binding domains (which purifies all antibodies that bind the antigen without regard to antibody class or isotype).

The main classes of serum immunoglobulins (e.g., IgG and IgM) share the same general structure, including overall amino acid composition and solubility characteristics. These general properties are sufficiently different from most other abundant proteins in serum, e.g., albumin and transferrin, that the immunoglobulins can be selected and enriched for on the basis of these differentiating physicochemical properties.

Physiochemical Fractionation Antibody Purification

Ammonium Sulfate Precipitation

Ammonium sulfate precipitation is frequently used to enrich and concentrate antibodies from serum, ascites fluid or cell culture supernatant. As the concentration of the lyotropic salt is increased in a sample, proteins and other macromolecules become progressively less soluble until they precipitate, i.e., the lyotropic effect is referred to as "salting out." Antibodies precipitate at lower concentrations of ammonium sulfate than most other proteins and components of serum.

At about 40 to about 50% ammonium sulfate saturation (100% saturation being equal to 4.32M), immunoglobulins precipitate while other proteins remain in solution. See, e.g., Harlow, E. and Lane, D. (1988). Antibodies: A Laboratory Manual. Cold Spring Harbor Laboratory Press, Cold Spring Harbor, N.Y. Gagnon, P. (1996). By way of example, an equal volume of saturated ammonium sulfate solution is slowly added to a neutralized antibody sample, followed by incubation for several hours at room temperature or 4° C. After centrifugation and removal of the supernatant, the antibody-pellet is dissolved in buffer, such as phosphate-buffered saline (PBS).

The selectivity, yield, purity and reproducibility of precipitation depends upon several factors including, but not limited to, time, temperature, pH and rate of salt addition. See, e.g., Gagnon, P. S. (1996). Purification Tools for Monoclonal Antibodies. Validated Biosystems. Tucson, AZ Ammonium sulfate precipitation may provide sufficient purification for some antibody applications, but often it is performed as a preliminary step before column chromatography or other purification method. Using partially-purified antibody samples can improve the performance and extend the life of affinity columns.

Suitable antibody precipitation reagents other than ammonium sulfate for antibody purification situations include, by way of example, octonoic acid, polyethylene glycol and ethacridine.

Numerous chemically-based, solid-phase chromatography methods have been adapted and optimized to achieve antibody purification in particular situations.

Ion Exchange Chromatography (IEC)

Ion exchange chromatography (IEC) uses positively or negatively charged resins to bind proteins based on their net charges in a given buffer system (pH). Conditions for IEC can be determined that bind and release the target antibody with a high degree of specificity, which may be especially important in commercial operations involving production of monoclonal antibodies. Conversely, conditions can be found that bind nearly all other sample components except antibodies. Once optimized, IEC is a cost-effective, gentle and reliable method for antibody purification.

Anion exchange chromatography uses a positively charged group immobilized to the resin. For example, weakly basic groups such as diethylamino ethyl (DEAE) or dimethylamino ethyl (DMAE), or strongly basic groups such as quaternary amino ethyl (Q) or trimethylammonium ethyl (TMAE) or quaternary aminoethyl (QAE)) can be used in anion exchange. Exemplary anion exchange media include, but are not limited to, GE Healthcare Q-Sepharose FF, Q-Sepharose BB, Q-Sepharose XL, Q-Sepharose HP, Mini Q. Mono Q, Mono P. DEAE Sepharose FF, Source 15Q, Source 30Q, Capto Q. Streamline DEAE, Streamline QXL; Applied Biosystems Poros HQ 10 and 20 um self pack, Poros HQ 20 and 50 um, Poros PI 20 and 50 um, Poros D 50 um; Tosohaas Toyopearl DEAE 650S M and C. Super Q 650, QAE 550C; Pall Corporation DEAE Hyper D, Q Ceramic Hyper D, Mustang Q membrane absorber: Merck KG2A Fractogel DMAE, FractoPrep DEAE, Fractoprep TMAE. Fractogel EMD DEAE, Fractogel EMD TMAE; Sartorious Sartobind Q membrane absorber.

Anion exchange is particularly useful for removing process-related impurities (e.g., host cell proteins, endogenous retrovirus and adventitious viruses such as parvovirus or pseudorabies virus. DNA, endotoxin and leached Protein A) as well as product-related impurities (e.g., dimer/aggregate). It can be used either in flow-through mode or in bind and elute mode, depending on the pI of the antibody and impurities to be removed. For example, flow-through mode is preferably used to remove impurities from antibodies having a pI above 7.5, e.g., most humanized or human IgG1 and IgG2 antibodies, because the impurities bind to the resin and the product of interest flows through. The column loading capacity, i.e., mass of antibody to mass of resin, can be quite high since the binding sites on the resin are occupied only by the impurities. Anion exchange chromatography in flow-through mode may be used as a polishing step in monoclonal antibody purification processes designed with two or three unit operations to remove residual impurities such as host cell protein, DNA, leached Protein A and a variety of viruses. By way of example, the operating pH is about 8 to about 8.2, with a conductivity of up to 10 mS/cm in the product load and equilibration and wash buffers.

Alternatively, bind and elute mode is preferably used to remove process-related and product-related impurities from antibodies having a pI in the acidic to neutral range, e.g., most humanized or human IgG4s. For bind-and-elute mode, the antibody product pool is first loaded onto an anion exchange column and the product of interest is then eluted with a higher salt concentration in a step or linear gradient, leaving the majority of impurities bound to the column. The impurities are eluted from the column during the cleaning or regeneration step. Generally, the operating pH should be above or close to the pI of the product in order to obtain a net negative charge or higher negative charge number on the surface of the antibody molecules, and, thus, to achieve a higher binding capacity during the chromatography step. Similarly, the ionic strength for the load is preferably in the low range and the pH is preferably less than pH 9.

Additionally, weak partitioning chromatography (WPC) may be used to enable a two chromatography recovery process comprising Protein A and anion exchange. Generally, the process is run isocratically (as with flow-through chromatography) but the conductivity and pH are chosen such that the binding of both the product and impurities are enhanced (in contrast to flow-through mode), attaining an antibody partition coefficient (Kp) between 0.1-20, and preferably between 1 and 3. Both antibody and impurities bind to the anion exchange resin, but the impurities are much more tightly bound than in flow-through mode, which can lead to an increase in impurity removal. Product yield in weak partitioning mode can be maximized by including a short wash at the end of the load, e.g., averaged 90% for clinical production.

Cation exchange chromatography uses a resin modified with negatively charged functional groups. For example, strong acidic ligands (e.g., sulfopropyl, sulfoethyl and sulfoisobutyl groups) or weak acidic ligands (e.g., carboxyl group) can be used in cation exchange. Exemplary cation exchange resins include, but are not limited to, GE Helalthcare SP-Sepharose FF. SP-Sepharose BB. SP-Sepharose XL, SP-Sepharose HP. Mini S. Mono S, CM Sepharose FF, Source 15S, Source 30S. Capto S, MacroCap SP. Streamline SP-XL. Streamline CST-1: Tosohaas Resins Toyopearl Mega Cap TI SP-550 EC, Toyopearl Giga Cap S-650M. Toyopearl 650S, M and C, Toyopeal SP650S, M. and C, Toyopeal SPS50C: TF Baker Resins Carboxy-Sulphon-5, 15 and 40 um. Sulfonic-5, 15, and 40 um; YMC BioPro S; Applied Biosystems Poros HS 20 and 50 um. Poros S 10 and 20 um; Pall Corp S Ceramic Hyper D, CM Ceramic Hyper D; Merck KGgA Resins Fractogel EMD $SO_3$, Fractogel EMD COO-, Fractogel EMD SE Hicap, Fracto Prep SO3: Eshmuno S; Biorad Resin Unosphere S; Sartorius Membrane Sartobind S membrane absorber.

Cation exchange chromatography is particularly suited for purification processes for many monoclonal antibodies with pI values ranging from neutral to basic, e.g., human or humanized IgG1 and IgG2 subclasses. In general, the antibody is bound onto the resin during the loading step and eluted through either increasing conductivity or increasing pH in the elution buffer. The most negatively charged process-related impurities such as DNA, some host cell protein, leached Protein A and endotoxin are removed in the load and wash fraction. Cation exchange chromatography can also reduce antibody variants from the target antibody product such as deamidated products, oxidized species and N-terminal truncated forms, as well as high molecular weight species.

The maximum binding capacity attained can be as high as >100 g/L of resin volume depending on the loading conditions, resin ligand and density, but impurity removal depends highly on the loading density. The same principles described for anion exchange chromatography regarding development of the elution program apply to cation exchange chromatography as well.

The development of elution conditions is linked to impurity removal and characteristics of the product pool that can be processed easily in the subsequent unit operation. Generally, a linear salt or pH gradient elution program can be conducted to determine the best elution condition. For example, linear gradient elution conditions may range from 5 mM to 250 mM NaCl at pH 6 and linear pH gradient elution runs may range from pH 6 to pH 8.

Immobilized Metal Chelate Chromatography (IMAC)

Immobilized metal chelate chromatography (IMAC) uses chelate-immobilized divalent metal ions (e.g., nickel Ni2+) to bind proteins or peptides that contain clusters of three or more consecutive histidine residues. This strategy can be particularly useful for purification of recombinant proteins that have been engineered to contain a terminal 6×His fusion tag. Mammalian IgGs are one of the few abundant proteins in serum (or monoclonal cell culture supernatant) that possess histidine clusters capable of being bound by immobilized nickel. Like IEC, IMAC conditions for binding and elution can be optimized for particular samples to provide gentle and reliable antibody purification. For example, IMAC may be used to separate AP- or HRP-labeled (enzyme-conjugated) antibody from excess, non-conjugated enzyme following a labeling procedure.

Hydrophobic Interaction Chromatography (HIC)

Hydrophobic interaction chromatography (HIC) separates proteins based on their hydrophobicity, and is complementary to other techniques that separate proteins based on charge, size or affinity. For example, a sample loaded on the HIC column in a high salt buffer which reduces solvation of the protein molecules in solution, thereby exposing hydrophobic regions in the sample protein molecules that consequently bind to the HIC resin. Generally, the more hydrophobic the molecule, the less salt is needed to promote binding. A gradient of decreasing salt concentration can then be used to elute samples from the HIC column. In particular, as the ionic strength decreases, the exposure of the hydrophilic regions of the molecules increases and molecules elute from the column in order of increasing hydrophobicity.

HIC in flow-through mode can be efficient in removing a large percentage of aggregates with a relatively high yield. HIC in bind-and-elute mode may provides effective separation of process-related and product-related impurities from antibody product. In particular, the majority of host cell protein, DNA and aggregates can be removed from the antibody product through selection of a suitable salt concentration in the elution buffer or use of a gradient elution method.

Exemplary HIC resins include, but are not limited to, GE Healthcare HIC Resins (Butyl Sepharose 4 FF, Butyl-S Sepharose FF, Octyl Sepharose 4 FF. Phenyl Sepharose BB. Phenyl Sepharose HP, Phenyl Sepharose 6 FF High Sub, Phenyl Sepharose 6 FF Low Sub, Source 15ETH, Source 15ISO, Source 15PHE, Capto Phenyl, Capto Butyl, Sreamline Phenyl); Tosohaas HIC Resins (TSK Ether 5PW (20 um and 30 um), TSK Phenyl 5PW (20 um and 30 um), Phenyl 650S, M, and C, Butyl 650S. M and C, Hexyl-650M and C, Ether-650S and M, Butyl-600M. Super Butyl-550C, Phenyl-600M; PPG-600M); Waters HIC Resins (YMC-Pack Octyl Columns-3, 5, 10P, 15 and 25 um with pore sizes 120, 200, 300 A, YMC-Pack Phenyl Columns-3, 5, 10P, 15 and 25 um with pore sizes 120, 200 and 300 A. YMC-Pack Butyl Columns-3, 5, 10P, 15 and 25 um with pore sizes 120, 200 and 300 A); CHISSO Corporation HIC Resins (Cellufine Butyl. Cellufine Octyl, Cellufine Phenyl); JT Baker HIC Resin (WP HI-Propyl (C3)); Biorad HIC Resins (Macroprep t-Butyl, Macroprep methyl); and Applied Biosystems HIC Resin (High Density Phenyl-HP2 20 um). For example, PPG 600-M is characterized by an exclusion limit molecular weight of approximately $8×10^5$ Dalton, a polypropylene glycol PPG ligand, a 45-90 μm particle size, hydrophobicity given by the relationship Ether>PPG>Phenyl, and Dynamic Binding capacity (MAb: Anti LH) of 38 mg/mL-gel.

In one embodiment, the disclosed purification processes employ hydrophobic interaction chromatography (HIC) as a polish purification step after affinity chromatography (e.g., Protein A) and mixed mode chromatography (e.g., hydroxyapatite). See, FIG. 1. Preferably, polypropylene glycol (PPG-600M) or Phenyl-600M is the HIC resin. In one embodiment, the elution is performed as a linear gradient (0-100%) from about 0.7 M to 0 M sodium sulfate in a 20 mM sodium phosphate, pH 7, buffer. Optionally the $OD_{280}$ of the effluent is monitored and a series of fractions, e.g., about one-third of the collection volume, is collected for further purity analysis. Preferably, the fractions collected include from 0.1 OD on the front flank to 0.1 OD on the rear flank.

Hydrophobic Charge Induction Chromatography (HCIC)

Hydrophobic charge induction chromatography (HCIC) is based on the pH-dependent behavior of ligands that ionize at low plH. This technique employs heterocyclic ligands at high densities so that adsorption can occur via hydrophobic interactions without the need for high concentrations of lyotropic salts. Desorption in HCIC is facilitated by lowering the pH to produce charge repulsion between the ionizable ligand and the bound protein. An exemplary commercial HCIC resin is MEP-Hypercel (Pall Corporation), which is a cellulose-based media with 4-mercaptoethyl pyridine as the functional group. The ligand is a hydrophobic moiety with an N-heterocyclic ring that acquires a positive charge at low pH.

Thiophilic Adsorption

Thiophilic adsorption is a highly selective type of protein-ligand interaction, combining the properties of hydrophobic interaction chromatography (IHIC) and ammonium sulfate precipitation (i.e., the lyotropic effect), that involves the binding of proteins to a sulfone group in close proximity to a thioether. In contrast to strict HIC, thiophilic adsorption depends upon a high concentration of lyotropic salt (e.g., potassium sulfate as opposed to sodium chloride). For example, binding is quite specific for a typical antibody sample that has been equilibrated with potassium sulfate. After non-bound components are washed away, the antibodies are easily recovered with gentle elution conditions (e.g., 50 mM sodium phosphate buffer, pH 7 to 8). Thiophilic Adsorbent (also called T-Gel) is 6% beaded agarose modified to contain the sulfone-thiocther ligand, which has a high binding capacity and broad specificity toward immunoglobulin from various animal species.

Affinity Purification of Antibodies

Affinity chromatography (also called affinity purification) makes use of specific binding interactions between molecules. Generally, a particular ligand is chemically immobilized or "coupled" to a solid support so that when a complex mixture is passed over the column, those molecules having specific binding affinity to the ligand become bound. After other sample components are washed away, the bound molecule is stripped from the support, resulting in its purification from the original sample.

Supports

Affinity purification involves the separation of molecules in solution (mobile phase) based on differences in binding interaction with a ligand that is immobilized to a stationary material (solid phase). A support or matrix in affinity purification is any material to which a biospecific ligand is covalently attached. Typically, the material to be used as an affinity matrix is insoluble in the system in which the target molecule is found. Usually, but not always, the insoluble matrix is a solid.

Useful affinity supports are those with a high surface-area to volume ratio, chemical groups that are easily modified for covalent attachment of ligands, minimal nonspecific binding properties, good flow characteristics and mechanical and chemical stability.

Immobilized ligands or activated affinity support chemistries are available for use in several different formats, including, e.g., cross-linked beaded agarose or polyacrylamide resins and polystyrene microplates.

Porous gel supports provide a loose matrix in which sample molecules can freely flow past a high surface area of immobilized ligand, which is also useful for affinity purification of proteins. These types of supports are usually sugar- or acrylamide-based polymer resins that are produced in solution (i.e., hydrated) as 50-150 μm diameter beads. The beaded format allows these resins to be supplied as wet slurries that can be easily dispensed to fill and "pack" columns with resin beds of any size. The beads are extremely porous and large enough that biomolecules (proteins, etc.) can flow as freely into and through the beads as they can between and around the surface of the beads. Ligands are covalently attached to the bead polymer (external and internal surfaces) by various means.

For example, cross-linked beaded agarose is typically available in 4% and 6% densities (i.e., a 1 ml resin-bed is more than 90% water by volume.) Beaded agarose may be suitable for gravity-flow, low-speed-centrifugation, and low-pressure procedures. Alternatively, polyacrylamide-based, beaded resins generally do not compress and may be used in medium pressure applications with a peristaltic pump or other liquid chromatography systems. Both types of porous support have generally low non-specific binding characteristics. A summary of the physical properties of these affinity chromatography resins is provided in Table 1 below.

TABLE 1

| Physical properties of affinity chromatography resins Physical properties of affinity chromatography resins | | | |
|---|---|---|---|
| Support | 4% crosslinked beaded agarose | 6% crosslinked beaded agarose | Acrylamide-azlactone polymer |
| Bead size | 45-165 μm | 45-165 μm | 50-80 μm |
| Exclusion limit | 20,000 kDa | 4,000 kDa | 2,000 kDa |
| Durability | crushes under high pressure | crushes under high pressure | sturdy (>100 psi, 6.9 bar) |
| Methods | gravity-flow or low-speed centrifugation | gravity-flow or low-speed centrifugation | FPLC Systems, HPLC, gravity flow |
| Coupling Capacity | medium | Medium | high |
| pH range | 3-11 | 3-11 | 1-13 |
| Form | pre-swollen | pre-swollen | dry or pre-swollen |

Magnetic particles are yet another type of solid affinity support. They are much smaller (typically 1-4 μm diameter), which provides the sufficient surface area-to-volume ratio needed for effective ligand immobilization and affinity purification. Affinity purification with magnetic particles is performed in-batch, e.g., a few microliters of beads is mixed with several hundred microliters of sample as a loose slurry. During mixing, the beads remain suspended in the sample solution, allowing affinity interactions to occur with the immobilized ligand. After sufficient time for binding has been given, the beads are collected and separated from the sample using a powerful magnet. Typically, simple benchtop procedures are done in microcentrifuge tubes, and pipetting or decanting is used to remove the sample (or wash solutions, etc.) while the magnetic beads are held in place at the bottom or side of the tube with a suitable magnet.

Magnetic particles are particularly well suited for high-throughput automation and, unlike porous resins, can be used in lieu of cell separation procedures.

Each specific affinity system requires its own set of conditions and presents its own peculiar challenges for a given research purpose. However, affinity purification generally involves the following steps:

1. Incubate crude sample with the affinity support to allow the target molecule in the sample to bind to the immobilized ligand;

2. Wash away non-bound sample components from the support; and

3. Elute (dissociate and recover) the target molecule from the immobilized ligand by altering the buffer conditions so that the binding interaction no longer occurs.

Ligands that bind to general classes of proteins (e.g., antibodies) or commonly used fusion protein tags (e.g., 6xHis) are commercially available in pre-immobilized formnns ready to use for affinity purification. Alternatively, more specialized ligands such as specific antibodies or antigens of interest can be immobilized using one of several commercially available activated affinity supports; for example, a peptide antigen can be immobilized to a support and used to purify antibodies that recognize the peptide.

Most commonly, ligands are immobilized or "coupled" directly to solid support material by formation of covalent chemical bonds between particular functional groups on the ligand (e.g., primary amines, sulfhydryls, carboxylic acids, aldehydes) and reactive groups on the support (see related article on Covalent Immobilization). However, indirect coupling approaches are also possible. For example, a GST-tagged fusion protein can be first captured to a glutathione support via the glutathione-GST affinity interaction and then secondarily chemically crosslinked to immobilize it. The immobilized GST-tagged fusion protein can then be used to affinity purify binding partner(s) of the fusion protein.

Binding and Elution Buffers for Affinity Purification

Most affinity purification procedures involving protein: ligand interactions use binding buffers at physiologic pH and ionic strength, such as phosphate buffered saline (PBS), particularly when the antibody:antigen or native protein: protein interactions are the basis for the affinity purification. Once the binding interaction occurs, the support is washed with additional butTer to remove non-bound components of the sample. Non-specific (e.g., simple ionic) binding interactions can be minimized by adding low levels of detergent or by moderate adjustments to salt concentration in the binding and/or wash buffer. Finally, clution buffer (e.g., 0.1 M glycine•HCl, pH 2.5-3.0) is added to break the binding interaction (without permanently affecting the protein structure) and release the target molecule, which is then collected in its purified form. Elution buffer can dissociate binding partners by extremes of pH (low or high), high salt (ionic strength), the use of detergents or chaotropic agents that denature one or both of the molecules, removal of a binding factor or competition with a counter ligand. In some cases, subsequent dialysis or desalting may be required to exchange the purified protein from elution buffer into a more suitable buffer for storage or downstream processing.

Additionally, some antibodies and proteins are damaged by low pH, so eluted protein fractions should be neutralized immediately by addition of ¹⁄₁₀th volume of alkaline buffer, e.g., 1 M Tris•HCl, pH 8.5. Other exemplary elution buffers for affinity purification of proteins are provided in Table 2 below.

TABLE 2

| Exemplary elution buffer systems for protein affinity purification | |
|---|---|
| Condition | Buffer |
| pH | 100 mM glycine•HCl, pH 2.5-3.0 |
| | 100 mM citric acid, pH 3.0 |
| | 50-100 mM triethylamine or triethanolamine, pH 11.5 |
| | 150 mM ammonium hydroxide, pH 10.5 |
| | 1M arginine, pH 4.0 |
| Ionic strength | 3.5-4.0 M magnesium chloride, pH 7.0 in 10 mM Tris |
| and/or | 5M lithium chloride in 10 mM phosphate buffer, pH 7.2 |
| chaotrophic | 2.5M sodium iodide, pH 7.5 |
| effects | 0.2-3.0 sodium thiocyanate |
| Denaturing | 2-6M guanidinc•HCl |
| | 2-8M urea |
| | 1% deoxycholate |
| | 1% SDS |
| Organic | 10% dioxane |
| | 50% ethylene glycol, pH 8-11.5 (also chaotropic) |
| Competitor | >0.1M counter ligand or analog |

Several methods of antibody purification involve affinity purification techniques. Exemplary approaches to affinity purification include precipitation with ammonium sulfate (crude purification of total immunoglobulin from other serum proteins); affinity purification with immobilized Protein A. G, A/G or L (bind to most species and subclasses of IgG) or recombinant Protein A, G. A/G, or L, derivatives in bind & elute mode; and affinity purification with immobilized antigen (covalently immobilized purified antigen to an affinity support to isolate specific antibody from crude samples) in bind & elute mode.

Protein A, Protein G and Protein L are three bacterial proteins whose antibody-binding properties have been well characterized. These proteins have been produced recombinantly and used routinely for affinity purification of key antiboxxly types from a variety of species. Most commercially-available, recombinant forms of these proteins have unnecessary sequences removed (e.g., the HSA-binding domain from Protein G) and are therefore smaller than their native counterparts. A genetically-engineered recombinant form of Protein A and Protein G, called Protein A/G, is also available. All four recombinant Ig-binding proteins are used routinely by researchers in numerous immunodetection and immunoaffinity applications.

To accomplish antibody purification, with Protein A. Protein G. Protein A/G are covalently immobilized onto a support, e.g., porous resins (such as beaded agarose) or magnetic beads. Because these proteins contain several antibody-binding domains, nearly every individual immobilized molecule, no matter its orientation maintains at least one functional and unhindered binding domain. Furthermore, because the proteins bind to antibodies at sites other than the antigen-binding domain, the immobilized forms of these proteins can be used in purification schemes, such as immunoprecipitation, in which antibody binding protein is used to purify an antigen from a sample by binding an antibody while it is bound to its antigen.

The high affinity of Protein A for the Fc region of IgG-type antibodies is the basis for the purification of IgG, IgG fragments and subclasses. Generally, Protein A chromatography involves passage of clarified cell culture supernatant over the column at pH about 6.0 to about 8.0, such that the antibodies bind and unwanted components, e.g., host cell proteins, cell culture media components and putative viruses, flow through the column. An optional intermediate wash step may be carried out to remove non-specifically bound impurities from the column, followed by elution of the product at pH about 2.5 to about pH 4.0. The elution step may be performed as a linear gradient or a step method or a combination of gradient and step. In one embodiment, the eluate is immediately neutralized with a neutralization buffer (e.g. 1 M Tris, pH 8), and then adjusted to a final pH 6.5 using, e.g., 5% hydrochloric acid or 1 M sodium hydroxide. Preferably, the neutralized eluate is filtered prior to subsequent chromatography. In one embodiment, the neutralized eluate is passed through a 0.2 µm filter prior to the subsequent hydroxyapatite chromatography step.

Because of its high selectivity, high flow rate and cost effective binding capacity and its capacity for extensive removal of process-related impurities such as host cell proteins, DNA, cell culture media components and endogenous and adventitious virus particles. Protein A chromatography is typically used as the first step in an antibody purification process. After this step, the antibody product is highly pure and more stable due to the elimination of proteases and other media components that may cause degradation.

There are currently three major types of Protein A resins, classified based on their resin backbone composition: glass or silica-based, e.g., AbSolute HiCap (NovaSep). Prosep vA, Prosep vA Ultra (Millipore); agarose-based, e.g., Protein A Sepharose Fast Flow, MabSelect and MabSelect SuRe (GE Healthcare); and organic polymer based. e.g., polystyrene-divinylbenzene Poros A and MabCapture (Applied Biosystems). Preferably, the Protein A resin is an agarose-based resin, i.e., MabSelect SuRe resin. All three resin types are resistant to high concentrations of guanidinium hydrochloride, urea, reducing agents and low pH.

The column bed height employed at large scale is between 10 and 30 cm, depending on the resin particle properties such as pore size, particle size and compressibility. Preferably, the column bed height is about 25 cm. Flow rate and column dimensions determine antibody residence time on the column. In one embodiment, the linear velocity employed for Protein A is about 150 to about 500 cm/hr, preferably about 200 cm/h to about 400 cm/h, more preferably about 200 cm/h to about 300 cm/h, and most preferably about 250 cm/h. Dynamic binding capacity ranges from 15-50 g of antibody per liter of resin, and depends on the flow rate, the particular antibody to be purified, as well as the Protein A matrix used. Preferably, the column is loaded with no more than 45 g of antibody per liter of resin. A method for determining dynamic binding capacities of Protein A resins has been described by Fahmer et al. Biotechnol Appl BioChem. 30:121-128 (1999). A lower loading flow rate may increase antibody residence time and promote higher binding capacity. It also results in a longer processing time per cycle, requires fewer cycles and consumes less buffer per batch of harvested cell culture fluid.

Other exemplary approaches to affinity purification include lectin affinity chromatography, which can be performed in flow-through mode (product with undesired glycosylation binds to support while product without undesired glycosylation passes through the support) or bind & elute mode (product with desired glycosylation binds to support while product without desired glycosylation passes through the support).

Proteins expressed in lower eukaryotes. e.g., *P. pastoris*, can be modified with O-oligosaccharides solely or mainly composed of mannose (Man) residues. Additionally, proteins expressed in lower eukaryotes, e.g., *P. pastoris*, can be modified with N-oligosaccharides. N-glycosylation in *P. pastoris* and other fungi is different than in higher eukaryotes. Even within fungi, N-glycosylation differs. In particular, the N-linked glycosylation pathways in *P. pastoris* are substantially different from those found in *S. cerevisiae*, with shorter Man(alpha 1,6) extensions to the core Man8GN2 and the apparent lack of significant Man(alpha 1,3) additions representing the major processing modality of N-linked glycans in *P. pastoris*. In some respects. *P. pastoris* may be closer to the typical mammalian high-mannose glycosylation pattern. Moreover. *Pichia* and other fungi may be engineered to produce "humanized glycoproteins" (i.e., genetically modify yeast strains to be capable of replicating the essential glycosylation pathways found in mammals, such as galactosylation.

Based on the desired or undesired O-linked and/or N-linked glycosylation modification of a protein product, one or more lectins can be selected for affinity chromatography in flow-through mode or bind & elute mode. For example, if a desired recombinant protein lacks particular O-linked and/or N-linked mannose modifications (i.e., desired protein is unmodified), a lectin that binds to mannose moieties, e.g., Con A. LCH. GNA, DC-SIGN and L-SIGN, can be selected for affinity purification in flow-through mode, such that the desired unmodified product passes through the support and is available for further purification or processing. Conversely, if a desired recombinant protein contains particular O-linked and/or N-linked mannose modifications (i.e., desired protein is unmodified), a lectin that binds to mannose moieties, e.g., Con A, LCH, GNA, DC-SIGN and L-SIGN, can be selected for affinity purification in bind & elute mode, such that the desired modified product binds to the support and the undesired unmodified product passes through. In the later example, the flow through can be discarded while the desired modified product is eluted from the support for further purification or processing. The same principle applies to recombinant protein products containing other glycosylation modifications introduced by the fungal expression system.

Another pseudo-affinity purification tool is 'mixed-mode' chromatography. As used herein, the term "mixed mode chromatography" refers to chromatographic methods that utilize more than one form of interactions between the stationary phase and analytes in order to achieve their separation, e.g., secondary interactions in mixed mode chromatography contribute to the retention of the solutes. Advantages of mixed mode chromatography include high selectivity, e.g., positive, negative and neutral substances could be separated in a single run, and higher loading capacity.

Mixed mode chromatography can be performed on ceramic or crystalline apatite media, such as hydroxyapatite (HA) chromatography and fluoroapatite (FA) chromatography. Other mixed mode resins include, but are not limited to. CaptoAdhere. Capto MMC (GE Healthcare); HEA Hypercel, and PPA Hypercel (Pall); and Toyopearl MX-Trp-650M (Tosoh BioScience). These chromatography resins provide biomolecule selectivity complementary to more traditional ion exchange or hydrophobic interaction techniques.

Ceramic hydroxyapatite $(Ca_5(PO_4)_3OH)_2$ is a form of calcium phosphate that can be used for the separation and purification of proteins, enzymes, nucleic acids, viruses and other macromolecules. Hydroxyapatite has unique separation properties and excellent selectivity and resolution. For example, it often separates proteins that appear to be homogeneous by other chromatographic and electrophoretic techniques. Ceramic hydroxyapatite (CHT) chromatography with a sodium chloride or sodium phosphate gradient elution may be used as polishing step in monoclonal antibody purification processes to remove dimers, aggregates and leached Protein A.

Exemplary hydroxyapatite (HA) sorbents of type I and type II are selected from ceramic and crystalline materials. HA sorbents are available in different particle sizes (e.g. type 1, Bio-Rad Laboratories). In an exemplary embodiment, the particle size of the HA sorbent is between about 10 µm and about 200 µm, between about 20 µm and about 100 µm or between about 30 µm and about 50 µm. In a particular example, the particle size of the HA sorbent is about 40 µm (e.g., CHT. Type 1).

Exemplary type 1 and type 11 fluoroapatite (FA) sorbents are selected from ceramic (e.g., bead-like particles) and crystalline materials. Ceramic FA sorbents are available in different particle sizes (e.g. type 1 and type 2, Bio-Rad Laboratories). In an exemplary embodiment the particle size of the ceramic FA sorbent is from about 20 µm to about 180 µm, preferably about 20 to about 100 µm, more preferably about 20 µm to about 80 µm. In one example, the particle size of the ceramic FA medium is about 40 µm (e.g., type 1 ceramic FA). In another example, the FA medium includes HA in addition to FA.

The selection of the flow velocity used for loading the sample onto the hydroxyapatite or fluoroapatite column, as well as the elution flow velocity depends on the type of hydroxyapatite or fluoroapatite sorbent and on the column geometry. In one exemplary embodiment, at process scale, the loading flow velocity is selected from about 50 to about 900 cm/h, from about 100 to about 500 cm/h, preferably from about 150 to about 300 cm/h and, more preferably, about 200 cm/h. In an exemplary embodiment, the pH of the elution buffer is selected from about pH 5 to about pH 9, preferably from about pH 6 to about pH 8, and more preferably about pH 6.5.

In one embodiment, the disclosed purification processes employ hydroxyapatite (HA) chromatography on CHT resin after protein A chromatography. Preferably, the elution is performed as a linear gradient (0-100%) from about 0 M to 1.5 M sodium chloride in a 5 mM sodium phosphate buffer at pH 6.5. The $OD_{280}$ of the effluent can be monitored. In one embodiment, during elution, a single fraction from 0.1 OD on the front flank to the peak maximum is collected and then a series of fractions, e.g., about one-third of the column volume, are collected from the peak maximum to 0.1 OD on the rear flank are collected for further purity analysis. In another preferred embodiment, the elution is performed as a linear gradient (0-100%) from about 5 mM to 0.25 M sodium phosphate buffer at pH 6.5. The $OD_{280}$ of the effluent can be monitored. During elution, fractions of ~½ CV can be collected from 0.1 OD on the front flank to 0.1 OD on the rear flank for further purity analysis.

Polyclonal antibodies (e.g., serum samples) require antigen-specific affinity purification to prevent co-purification of non-specific immunoglobulins. For example, generally only 2-5% of total IgG in mouse serum is specific for the antigen used to immunize the animal. The type(s) and degree of purification that are necessary to obtain usable antibody depend upon the intended application(s) for the antibody. However, monoclonal antibodies that were developed using cell lines, e.g., hybridomas or recombinant expression systems, and produced as ascites fluid or cell culture supernatant can be fully purified without using an antigen-specific affinity method because the target antibody is (for most practical purposes) the only immunoglobulin in the production sample.

Monitoring for Impurities

Profiling of impurities in biopharmaceutical products and their associated intermediates and excipients is a regulatory expectation. See, e.g., US Food and Drug Administration *Genotoxic and Carcinogenic Impurities in Drug Substanmces and Products: Recommended* Approaches. This guidance provides recommendations on how to evaluate the safety of these impurities and exposure thresholds. The European Medicines Agency's (EMEA committee for Medicinal Products for Human Use (CHMP) also published the *Guideline on the Limits of Genotoxic Impurities*, which is being applied by European authorities for new drug products and in some cases also to drug substances in drug development. These guidelines augment the International Conference on Harmonization (ICH) guidances for industry: *Q3A(R2) Impurities in New Drug Substances, Q3B(R2) Impurities in New Drug Produs, and Q3C(R3) Impurities: Residual Solvents* that address impurities in a more general approach.

Although some impurities are related to the drug product (i.e., product-associated variant), others are added during synthesis, processing, and manufacturing. These impurities fall into several broad classes: product-associated variants; process-related substances introduced upstream; residual impurities throughout the process; process-related residual impurities introduced downstream; and residual impurities introduced from disposables.

As used herein, "product-associated variant" refers to a product other than the desired product (e.g., the desired multi-subunit complex) which is present in a preparation of the desired product and related to the desired product. Exemplary product-associated variants include truncated or elongated peptides, products having different glycosylation than the desired glycosylation (e.g., if an aglycosylated product is desired then any glycosylated product would be considered to be a product-associated variant), complexes having abnormal stoichiometry, improper assembly, abnormal disulfide linkages, abnormal or incomplete folding, aggregation, protease cleavage, or other abnormalities. Exemplary product-associated variants may exhibit alterations in one or more of molecular mass (e.g., detected by size exclusion chromatography), isoelectric point (e.g., detected by isoelectric focusing), electrophoretic mobility (e.g., detected by gel electrophoresis), phosphorylation state (e.g., detected by mass spectrometry), charge to mass ratio (e.g., detected by mass spectrometry), mass or identity of proteolytic fragments (e.g., detected by mass spectrometry or gel electrophoresis), hydrophobicity (e.g., detected by HPLC), charge (e.g., detected by ion exchange chromatography), affinity (e.g., in the case of an antibody, detected by binding to protein A, protein G, and/or an epitope to which the desired antibody binds), and glycosylation state (e.g., detected by lectin binding affinity). Where the desired protein is an antibody, the term product-associate variant may include a glyco-heavy variant and/or half antibody species (described below).

Exemplary product-associated variants include variant forms that contain aberrant disulfide bonds. For example, most IgG1 antibody molecules are stabilized by a total of 16 intra-chain and inter-chain disulfide bridges, which stabilize the folding of the IgG domains in both heavy and light chains, while the inter-chain disulfide bridges stabilize the association between heavy and light chains. Other antibody types likewise contain characteristic stabilizing intra-chain and inter-chain disulfide bonds. Further, some antibodies (including Ab-A disclosed herein) contain additional disulfide bonds referred to as non-canonical disulfide bonds. Thus, aberrant inter-chain disulfide bonds may result in abnormal complex stoichiometry, due to the absence of a stabilizing covalent linkage, and/or disulfide linkages to additional subunits. Additionally, aberrant disulfide bonds (whether inter-chain or intra-chain) may decrease structural stability of the antibody, which may result in decreased activity, decreased stability, increased propensity to form aggregates, and/or increased immunogenicity. Product-associated variants containing aberrant disulfide bonds may be detected in a variety of ways, including non-reduced denaturing SDS-PAGE, capillary electrophoresis, cIEX, mass spectrometry (optionally with chemical modification to produce a mass shift in free cysteines), size exclusion chromatography, HPLC, changes in light scattering, and any other suitable methods known in the art. See, e.g., The Protein Protocols Handbook 2002, Part V, 581-583, DOI: 10.1385/1-59259-169-8:581.

Generally, dialysis, desalting and diafiltration can be used to exchange antibodies into particular buffers and remove undesired low-molecular weight (MW) components. In particular, dialysis membranes, size-exclusion resins, and diafiltration devices that feature high-molecular weight cut-offs (MWCO) can be used to separate immunoglobulins (>140 kDa) from small proteins and peptides. See, e.g., Grodzki, A. C. and Berenstein, E. (2010). Antibody purification: ammonium sulfate fractionation or gel filtration. In: C. Oliver and M. C. Jamur (eds.), Immunocytochemical Methods and Protocols, Methods in Molecular Biology, Vol. 588:15-26. Humana Press.

Size-exclusion chromatography can be used to detect antibody aggregates, monomer, and fragments. In addition, size-exclusion chromatography coupled to mass spectrometry may be used to measure the molecular weights of antibody; antibody conjugates, and antibody light chain and heavy chain.

Exemplary size exclusion resins for use in the purification and purity monitoring methods include TSKgel G3000SW and TSKgel G3000SWx1 from Tosoh Biosciences (Montgomeryville, PA, USA); Shodex KW-804, Protein-Pak 300SW, and BioSuite 250 from Waters (Milford, MA, USA); MAbPac™ SEC-1 and MAbPac TM SCX-10 from Thermo Scientific (Sunnyvale, California USA).

In one embodiment, size exclusion chromatography is used to monitor impurity separation during the purification process. By way of example, an equilibrated TSKgel GS3000SW 17.8×300 mm column connected with a TSKgel Guard SW×16×40 mm from Tosoh Bioscience (King of Prussia, PA) may be loaded with sample, using a SE-HPLC buffer comprising 100 mM sodium phosphate, 200 mM sodium chloride pH 6.5 as a mobile phase with a flow rate of 0.5 mL/min in isocratic mode. Using an Agilent (Santa Clara, CA) 1200 Series HPLC with UV detection instrument, absorbance at UV 215 nm can be monitored. Samples can then be collected and diluted to a desired concentration, e.g., 1 mg/mL. The diluted sample of a fraction thereof, e.g., 30 μL, can then be loaded onto the SE-HPLC column. Preferably, column performance is monitored using gel filtration standards (e.g., BioRad).

Product-associated variants include glycovariants. As used herein, "glycovariant" refers to a glycosylated product-associated variant sometimes present in antibody preparations and which contains at least a partial Fe sequence. The glycovariant contains glycans covalently attached to polypeptide side chains of the desired protein. The glycovariant may be "glyco-heavy" or "glyco-light" in comparison to the desired protein product, i.e., contains additional glycosylation modifications compared to the desired protein or contains less glycosylation modifications than the desired protein, respectively. Exemplary glycosylation modifications include, but are not limited to, N-linked glycosylation. O-linked glycosylation, C-glycosylation and phosphoglycosylation.

The glycovariant is characterized by increased or decreased electrophoretic mobility observable by SDS-PAGE (relative to a normal polypeptide chain), lectin binding affinity, binding to an anti-Fe antibody, and apparent higher or lower molecular weight of antibody complexes containing the glycovariant as determined by size exclusion chromatography. See, e.g., U.S. Provisional Application Ser. No. 61/525,307, filed Aug. 31, 2011, which is incorporated by reference herein in its entirety.

As used herein "glycosylation impurity" refers to a material that has a different glycosylation pattern than the desired recombinant protein. The glycosylation impurity may contain the same or different primary, secondary, tertiary and/or quaternary structure as the desired recombinant protein. Therefore, a glycovariant is a type of glycosylation impurity.

Analytical methods for monitoring glycosylation of mAbs are important because bioprocess conditions can cause, e.g., variation in high mannose type, truncated forms, reduction of tetra-antennary and increase in tri- and biantennary structures, less sialylated glycans and less glycosylation. The presence of glycovariants in a sample may be monitored using analytical means known in the art, such as glycan staining or labeling, glycoproteome and glycome analysis by mass spectrometry and/or glycoprotein purification or enrichment. In one embodiment, glycovariants are analyzed using lectin kinetic binding assays, e.g., light interferometry (which may be performed using a ForteBio Octet®), dual polarization interferometry (which may be performed using a Farfield AnaLight®), static light scattering (which may be performed using a Wyatt DynaPro NanoStar™), dynamic light scattering (which may be performed using a Wyatt DynaPro NanoStar™), composition-gradient multi-angle light scattering (which may be performed using a Wyatt Calypso II), surface plasmon resonance (which may be performed using ProteOn XPR36 or Biacore T100), ELISA, chemoelectroluminescent ELISA, far western analysis, chemoluminescence (which may be performed using a MesoScale Discovery) or other lectin kinetic binding assay.

In one embodiment, glycan staining or labeling is used to detect glycovariants. For example, glycan sugar groups can be chemically restructured with periodic acid to oxidize vicinal hydroxyls on sugars to aldehydes or ketones so that they are reactive to dyes, e.g., periodic acid-Schiff (PAS) stain, to detect and quantify glycoproteins in a given sample. Periodic acid can also be used to make sugars reactive toward crosslinkers, which can be covalently bound to labeling molecules (e.g., biotin) or immobilized support (e.g., streptavidin) for detection or purification.

In another embodiment, mass spectrometry is used to identify and quantitate glycovariants in a sample. For example, enzymatic digestion may be used to release oligosaccharides from the immunoglycoprotein, where the oligosaccharide is subsequently derivatized with a fluorescent modifier, resolved by normal phase chromatography coupled with fluorescence detection, and analyzed by mass spectrometry (e.g., MALDI-TOF). The basic pipeline for glycoproteomic analysis includes glycoprotein or glycopeptides enrichment, multidimensional separation by liquid chromatography (LC), tandem mass spectrometry and data analysis via bioinformatics.

Spectrometric analysis can be performed before or after enzymatic cleavage of glycans by, e.g., endoglycanase H (endo H) or peptide-N4-(N-acetyl-beta-glucosaminyl)asparagine amidase (PNGase), depending on the experiment.

Additionally, quantitative comparative glycoproteome analysis may be performed by differential labeling with stable isotope labeling by amino acids in cell culture (SI-LAC) reagents. Moreover, absolute quantitation by selected reaction monitoring (SRM) can be performed on targeted glycoproteins using isotopically labeled, "heavy" reference peptides.

In one embodiment, lectins are used to detect and analyze glycovariants of the desired recombinant protein during the purification process. Lectins are glycan-binding proteins have high specificity for distinct sugar moieties. A non-limiting list of commercially available lectins is provided in Table 3 below.

TABLE 3

Exemplary commercially available lectins.

| Lectin Symbol | Lectin Name | Source | Ligand motif |
|---|---|---|---|
| Mannose binding lectins | | | |
| ConA | Concanavalin A | *Canavalia ensiformis* | α-D-mannosyl and α-D-glucosyl residues branched α-mannosidic structures (high α-mannose type, or hybrid type and biantennary complex type N-Glycans) |
| LCH | Lentil lectin | *Lens culinaris* | Fucosylated core region of bi- and triantennary complex type N-Glycans |
| GNA | Snowdrop lectin | *Galanthus nivalis* | α 1-2, α 1-3 and α 1-6 linked high mannose structures |
| DC-SIGN | Dendritic Cell-Specific Intercellular adhesion molecule-3-Grabbing Non-integrin | Human Murine | Calcium-dependent mannose-type carbohydrates |
| L-SIGN | Liver/lymph node-specific intercellular adhesion molecule-3-grabbing integrin | Human Murine | Calcium-dependent mannose-type carbohydrates |
| Galactose/N-acetylgalactosamine binding lectins | | | |
| RCA | Ricin, Ricinus communis Agglutinin, RCA 120 | *Ricinus communis* | Galβ1-4GlcNAcβ1-R |
| PNA | Peanut agglutinin | *Arachis hypogaea* | Galβ1-3GalNAcα1-Ser/Thr (T-Antigen) |
| AIL | Jacalin | *Artocarpus integrifolia* | (Sia)Galβ1-3GalNAcα1-Ser/Thr (T-Antigen) |
| VVL | Hairy vetch lectin | *Vicia villosa* | GalNAcα-Ser/Thr (Tn-Antigen) |
| N-acetylglucosamine binding lectins | | | |
| WGA | Wheat Germ Agglutinin, WGA | *Triticum vulgaris* | GlcNAcβ1-4GlcNAcβ1-4GlcNAc, Neu5Ac (sialic acid) |
| N-acetylneursminic acid binding lectins | | | |
| SNA | Elderberry lectin | *Sambucus nigra* | Neu5Acα2-6Gal(NAc)-R |
| MAL | *Maackia amurensis leukoagglutinin* | *Maackia amurensis* | Neu5Ac/Gcα2,3Galβ1,4Glc(NAc) |
| MAH | *Maackia amurensis hemoagglutinin* | *Maackia amurensis* | Neu5Ac/Gcα2,3Galβ1,3(Neu5Acαa2,6)GalNac |
| Fucose binding lectins | | | |
| UEA | *Ulex europaeus* agglutinin | *Ulex europaeus* | Fucα1-2Gal-R |
| AAL | *Aleuria aurantia* lectin | *Aleuria aurantia* | Fucα1-2Galβ1-4(Fucα1-3/4)Galβ1-4GlcNAc, R2-GlcNAcβ1-4(Fucα1-6)GlcNAc-R1 |

In one embodiment, a sample obtained from the fermentation process, e.g., during the run or after the run is completed, is subject to lectin binding assay to detect the amount and/or type of glycosylated impurities in the sample(s). Similarly, in other embodiments, the purification process includes detecting the amount and/or type of glycosylated impurities in a sample from which the desired recombinant protein is purified. For example, in a particular embodiment, a portion of the eluate or a fraction thereof from at least one chromatographic step in the purification process may be contacted with a lectin.

The level of lectin binding often correlates with the level of the product-associated glycovariant impurity present in the eluate or a fraction thereof (based on conventional size exclusion chromatography methods), such that one or more fractions of the eluate can be selected for further purification and processing based on the content of glycovariant impurities, e.g., select fractions of the eluate with less than 10%/o glycovariant for further chromatographic purification. In some embodiments, multiple lectins (i.e., two or more lectins) may be used to monitor purity of the product associated glycovariant impurities.

In an alternate embodiment, certain samples or eluate or fractions thereof are discarded based on the amount and/or type of detected glycosylated impurities. In yet another embodiment, certain samples or fractions are treated to reduce and/or remove the glycosylated impurities based on the amount and/or type of detected glycosylated impurities. Exemplary treatment includes one or more of the following: (i) addition of an enzyme or other chemical moiety that removes glycosylation. (ii) removal of the glycosylated impurities by effecting one or more lectin binding steps, (iii) effecting size exclusion chromatography to remove the glycosylated impurities.

In a particular embodiment, the lectin is conjugated to a probe and then immobilized to a support. See FIG. 2. The support may be in batch or packed into a column, e.g., for HIPLC. Exemplary probes include biotin, alkaline phosphatase (AP), horseradish peroxidase (HRP), luciferase, fluorescein (fluorescein isothiocyanate, FITC) and rhodamine (tetramethyl rhodamine isothiocyanate. TRITC), green fluorescent protein (GFP) and phycobiliproteins (e.g., allophycocyanin, phycocyanin, phycoerythrin and phycoerythrocyanin). Exemplary supports include avidin, streptavidin, NeutrAvidin (deglycosylated avidin) and magnetic beads. It should be noted that the invention is not limited by coupling chemistry. Preferably, the lectin is biotinylated and immobilized onto a streptavidin sensor.

Standard protein-protein interaction monitoring processes may be used to analyze the interaction between lectin and glycosylation impurities in samples from various steps of the purification process. Exemplary protein-protein interaction monitoring process include, but are not limited to, light interferometry (which may be performed using a ForteBio Octet®), dual polarization interferometry (which may be performed using a Farfield AnaLight®), static light scattering (which may be performed using a Wyatt DynaPro NanoStar™), dynamic light scattering (which may be performed using a Wyatt DynaPro NanoStar™), composition-gradient multi-angle light scattering (which may be performed using a Wyatt Calypso II), surface plasmon resonance (which may be performed using ProteOn XPR36 or Biacore T100), ELISA, chemoelectroluminescent ELISA, far western analysis, chemoluminescence (which may be performed using a MesoScale Discovery) or other lectin kinetic binding assay.

Light interferometry is an optical analytical technique that analyzes the interference pattern of white light reflected from two surfaces (a layer of immobilized protein on the biosensor tip, and an internal reference layer) to measure biomolecular interactions in real-time based on a shift in the interference pattern (i.e., caused by a change in the number of molecules bound to the biosensor tip), thereby providing information about binding specificity, rates of association and dissociation, or concentration.

Dual polarization interferometry is based on a dual slab wave guide sensor chip that has an upper sensing wave guide as well as a lower optical reference wave guide lit up with an alternating orthogonal polarized laser beam. Two differing wave guide modes are created-specifically, the transverse Magnetic™ mode and the transverse electric (TE) mode. Both modes generate an evanescent field at the top sensing wave guide surface and probe the materials that contact with this surface. As material interacts with the sensor surface, it leads to phase changes in interference fringes. Then, the interference fringe pattern for each mode is mathematically resolved into RI and thickness values. Thus, the sensor is able to measure extremely subtle molecular changes on the sensor surface.

Static light scattering (SLS) is a non-invasive technique whereby an absolute molecular mass of a protein sample in solution may be experimentally determined to an accuracy of better than 5% through exposure to low intensity laser light (690 nm). The intensity of the scattered light is measured as a function of angle and may be analyzed to yield the molar mass, root mean square radius, and second virial coefficient (A2). The results of an SLS experiments can be used as a quality control in protein preparation (e.g. for structural studies) in addition to the determination of solution oligomeric state (monomer/dimcr etc.). SLS experiments may be performed in either batch or chromatography modes.

Dynamic light scattering (also known as quasi-elastic light scattering. QELS, or photon correlation spectroscopy. PCS) is a technique for measuring the hydrodynamic size of molecules and submicron particles based on real-time intensities (compared to time-average intensities, as measured by static light scattering). Fluctuations (temporal variation, typically in a us to ms time scale) of the scattered light from a particle in a medium are recorded and analyzed in correlation delay time domain. The particles can be solid particles (e.g., metal oxides, mineral debris, and latex particles) or soft particles (e.g., vesicles and micelles) in suspension, or macromolecular chains (e.g., synthetic polymers and biomaterials) in solution. Since the diffusion rate of particles is determined by their sizes in a given environment, information about their size is contained in the rate of fluctuation of the scattered light.

The scattering intensity of a small molecule is proportional to the square of the molecular weight. As such, dynamic and static light scattering techniques are very sensitive to the onset of protein aggregation and other changes in protein structure arising from subtle changes in conditions.

Composition-gradient multi-angle light scattering (CG-MALS) employs a series of unfractionated samples of different composition or concentration in order to characterize macromolecular interactions such as reversible self- and hetero-association of proteins, reaction rates and affinities of irreversible aggregation, or virial coefficients. Such measurements provide information about specific reversible complex binding (e.g., $K_d$, stoichiometry, self and/or heteroassociations), non-specific interactions (e.g., self- and cross-virial coefficients), aggregation and other time-dependent reactions (e.g., stop-flow kinetics and t) and Zimm plots (e.g., concentration gradients for determining $M_W$, $A_2$, $A_3$ (second and third virial coefficients), or $r_g$).

The surface plasmon resonance (SPR) phenomenon occurs when polarized light, under conditions of total internal reflection, strikes an electrically conducting (e.g., gold) layer at the interface between media of different refractive index (i.e., glass of a sensor surface (high refractive index) and a buffer (low refractive index)). A wedge of polarized light, covering a range of incident angles, is directed toward the glass face of the sensor surface. An electric field intensity (i.e., evanescent wave), which is generated when the light strikes the glass, interacts with, and is absorbed by, free electron clouds in the gold layer, generating electron charge density waves called plasmons and causing a reduction in the intensity of the reflected light. The resonance angle at which this intensity minimum occurs is a function of the refractive index of the solution close to the gold layer on the opposing face of the sensor surface. Reflected light is detected within a monitoring device, e.g., ProteOn XPR36 or Biacore system. The kinetics (i.e. rates of complex formation ($k_a$) and dissociation ($k_d$)), affinity (e.g., $K_D$), and concentration information can be determined based on the plasmon readout.

Information obtained from these and other protein-protein interaction monitoring processes can be used to, e.g., quantify binding affinity and stoichiometry of enzyme/inhibitor or antibody/antigen interactions or glycoprotein/lectin interactions; study the impact of small molecules on protein-protein interactions; adjust buffer parameters to improve formulation stability and viscosity; optimize antibody purification and understand the effects of large excipients on formulations; quantify impact of solvent ionic strength, pH, or excipients on polymerization or protein associations; measure kinetics of self-assembly and aggregation; and characterize macromolecular binding affinity and associated complex stoichiometry over a wide range of buffer compositions, time, and temperature scales.

In a preferred embodiment, the level of lectin binding (which correlates with the amount of glycovariant impurity) is determined using light interferometry. e.g., Octet analysis instruments (FortéBIO).

Exemplary process-related impurities introduced upstream include nucleic acids (e.g., DNA and RNA) and host cell proteins (HCP) that are unwanted cell components found with the protein of interest after cell lysis. These process-related impurities also include antibiotics that are added upstream to the cell-culture media to control bacterial contamination and maintain selective pressure on the host organisms. Exemplary antibiotics include kanamycin, ampicillin, penicillin, amphotericin B, tetracyline, gentamicin sulfate, hygromycin B, and plasmocin.

Exemplary residual impurities incurred throughout the process include process enhancing agents or catalysts, which are added throughout the process to make some of the steps more efficient and increase yield of the product. For example, guanidine and urea are added for solubilization of the fermentation output, and glutathione and dithiothreitol (DTT) are used during reduction and refolding of proteins.

Exemplary process-related impurities introduced downstream include chemicals and reagents (e.g., alcohols and glycols) required for chromatographic purification of target proteins that must be cleared from the process, as well as surfactants (e.g., Triton-X, Pluronic, Antifoam-A, B, C, Tween, or Polysorbate) that are added during downstream processing to aid in separating the protein, peptide, and nucleic acids from the process stream by lowering the interfacial tension by adsorbing at the liquid-liquid interface.

Exemplary residual impurities introduced from disposables include "extractables," which are compounds that can be extracted from a component under exaggerated conditions (e.g., harsh solvents or at elevated temperatures) and have the potential to contaminate the drug product, and "leachables," which are compounds that leach into the drug product formulation from the component as a result of direct contact with the formulation under normal conditions or sometimes at accelerated conditions. Leachables may be a subset of extractables. Extractables must be controlled to the extent that components used are appropriate. Leachables must be controlled so that the drug products are not adulterated.

To further articulate the invention described above, we provide the following non-limiting examples.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1: Ab-A Purification and Recovery

This example illustrates that the purity of recombinant antibodies generated in *P. pastoris* was improved by using a series of primary recovery and chromatographic purification processes. An overview of the purification method is shown in FIG. 1. These methods can be used to purify and recover a variety of antigen-specific antibodies expressed in different systems.

*P. pastoris* cells containing stably integrated sequences encoding the Ab-A heavy and light chains (corresponding to SEQ ID NO:54 and SEQ ID NO:52 as listed in US 20120294797, which is incorporated by reference in its entirety) linked to a secretion signal were cultured and antibody expression was induced.

Whole fermentation broth was treated with ethylene diamine tetraacetic acid (EDTA) to 3 mM final concentration and with a flocculating agent. Cells and flocculated debris were removed from the harvested broth by centrifugation, followed by clarification through depth and 0.2 μm filters.

The clarified broth was then applied to a column of MabSelect SuRe (GE Healthcare Life Sciences) resin to capture Ab-A by Protein A affinity chromatography. Chromatography was performed at ambient temperature. A column of 25 cm bed height was sanitized with 0.1 M sodium hydroxide and then equilibrated with 20 mM sodium phosphate. 150 mM sodium chloride, pH 6.0 buffer ("PrA equilibration buffer") prior to loading. The column was loaded to a capacity of not more than 45 g Ab-A per L resin at 250 cm/hr linear velocity, and then operated at the same linear velocity throughout. Following application of the load, the column was rinsed for 5 column volumes (CV) with equilibration buffer, and then washed for 5 CV with 20 mM sodium phosphate, 10 mM EDTA, 1 M sodium chloride, pH 6.0 to remove loosely bound materials. The column was rinsed with another 5 CV equilibration buffer to remove wash components, and then bound Ab-A was desorbed with 1 M arginine, pH 4.0 ("PrA elution buffer"). The elution step was carried out as a linear gradient from 0-100% elution buffer over 3 CV followed by elution at 100% elution buffer for another 3 CV. The $OD_{280}$ of the effluent was monitored, and eluate was collected from 1 OD on the front flank to 1 OD on the rear flank. The eluate was collected in a vessel pre-loaded with 0.15 CV of 1 M Tris, pH 8.0 ("PrA neutralization buffer"). Following collection the vessel's contents were mixed and its pH value determined, prior to final adjustment to pH 6.5 using either 5% hydrochloric acid or 1 M sodium hydroxide as necessary. The neutralized eluate was 0.2 µm filtered, then forwarded on to the hydroxyapatite chromatography step. Following product elution, the capture column was stripped with 20 mM sodium acetate, pH 3.6 for 3 CV, cleaned with 0.2 M sodium hydroxide for 3CV, and rinsed with equilibration buffer for 3 CV prior to storage in 20% ethanol.

Figure 5A:
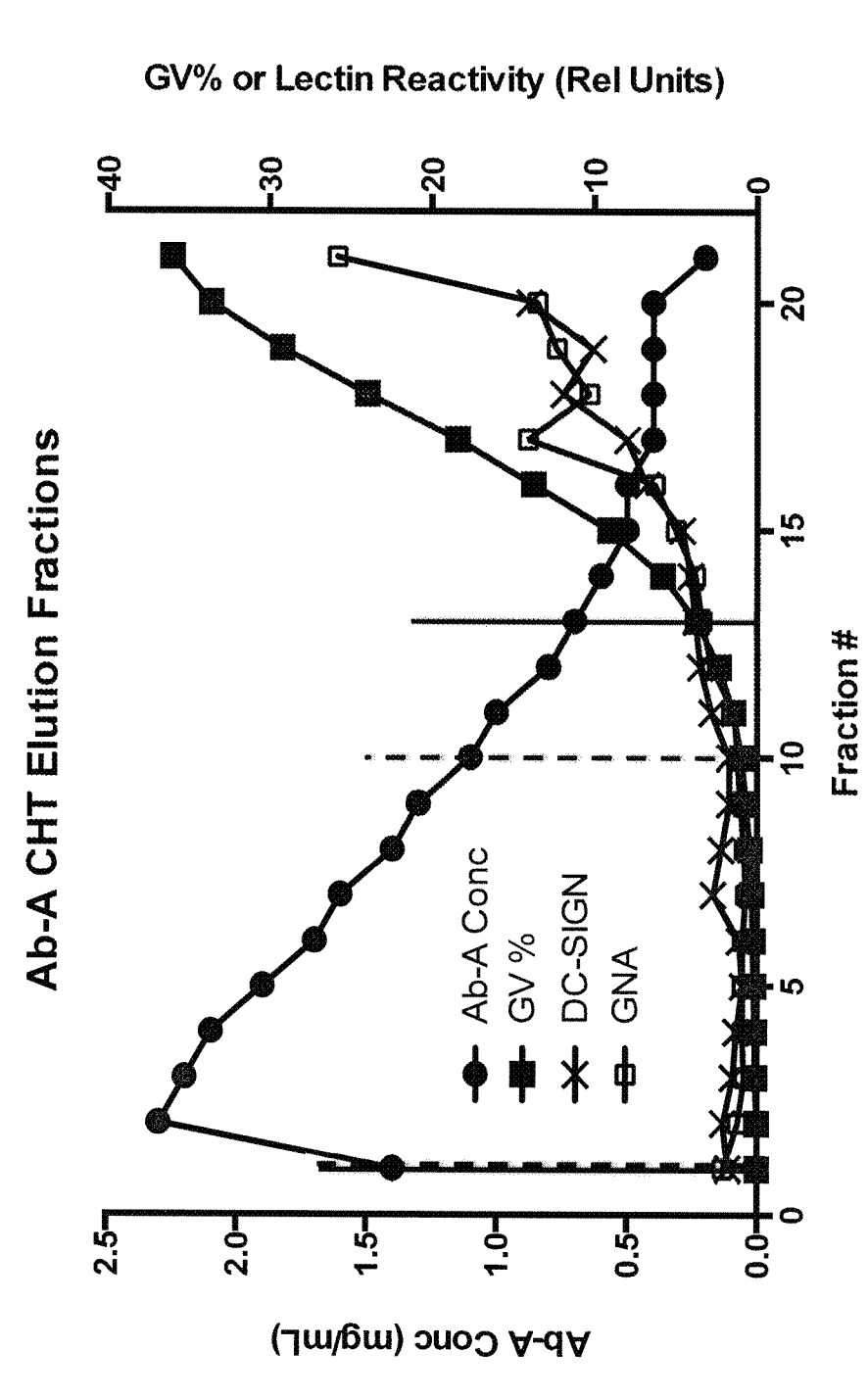

Intermediate purification of Ab-A used mixed mode chromatography on ceramic hydroxyapatite (CHT, Type 1, 40 µm) resin. This step was carried out at ambient temperature and at not more than 200 cm/hr linear velocity throughout. Prior to each run the column was sanitized using 3 CV of 1 M sodium hydroxide, stripped with 3 CV 500 mM sodium phosphate, pH 6.5 ("strip buffer"), and equilibrated with at least 3 CV 5 mM sodium phosphate, pH 6.5 ("CHT equilibration buffer"). The CHIT load was prepared by diluting the filtered, neutralized capture eluate with CHT equilibration buffer to a conductivity of not more than 4 mS/cm. The CHT load was then applied to the equilibrated column after passing through a 0.2 µm filter placed ahead of the column. Following loading, the column was washed with 5 CV of CHT equilibration buffer and then eluted with a 20 CV linear gradient from 0-100°%5 mM sodium phosphate, 1.5 M sodium chloride, pH 6.5 ("CHT elution buffer"). The ODaoof the effluent was monitored, and a single fraction from 0.1 OD on the front flank to the peak maximum was collected. Thereafter, a series of fractions of $\sim \frac{1}{3}^{rd}$ CV were collected from the peak maximum to 0.1 OD on the rear flank. The fractions were analyzed for purity (see FIG. 3), and a set of contiguous fractions (including the first, larger fraction) were combined to achieve a CHT Pool of desired purity and reduced glycovariant content (see FIG. 4 and FIG. 5). After elution, the CHT column was stripped with 3 CV 500 mM sodium phosphate. pH 6.5 ("CHT strip buffer"), cleaned in place with 5 CV 1 M sodium hydroxide, and rinsed with 3 CV 0.1 M sodium hydroxide storage solution.

Figure 6A:
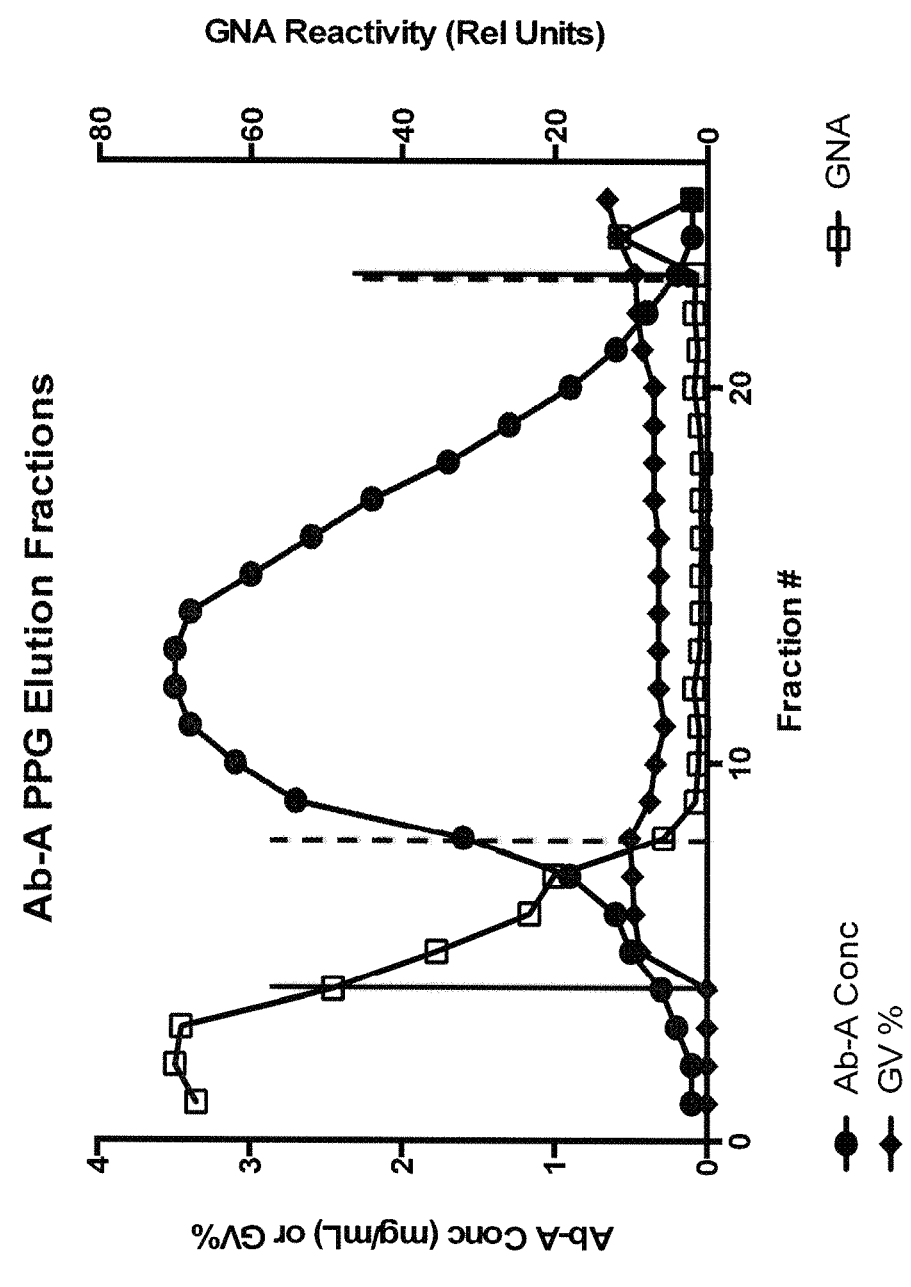

Polish purification of Ab-A used hydrophobic interaction chromatography (HIC) on polypropylene glycol (PPG-) 600M resin. This step was carried out at ambient temperature and at not more than 200 cm/hr linear velocity throughout. Prior to each run the column was sanitized using 3 CV of 0.5 M sodium hydroxide, stripped with 3 CV water, and equilibrated with at least 3 CV 20 mM sodium phosphate, 0.7 M sodium sulfate, pH 7.0 ("HIC equilibration buffer"). The HIC load was prepared by adjusting 0.2 µm filtered CHT Pool to a conductivity of at least 77.5 mS/cm using 20 mM sodium phosphate, 1.1 M sodium sulfate, pH 7.0 ("HIC dilution buffer"). The HIC load was then applied to the equilibrated column after passing through a 0.2 µm filter placed ahead of the column. Following loading, the column was washed with 5 CV of HIC equilibration buffer and then eluted with a 20 CV linear gradient from 0-100% 20 mM sodium phosphate, pH 7.0 ("HIC elution buffer"). The $OD_{280}$ of the effluent was monitored, and a series of fractions of $\sim \frac{1}{3}^{rd}$ CV were collected from 0.1 OD on the front flank to 0.1 OD on the rear flank. The fractions were analyzed for purity (see FIG. 6), and a set of contiguous fractions were combined to form a HIC Pool of desired purity and reduced glycovariant content. After elution, the HIC column was stripped with 3 CV water, cleaned in place with 6 CV 0.5 M sodium hydroxide (with a 60-120 min pause between the first 3 and last 3 CV), rinsed with 3 CV water, and transferred into 0.1 M sodium hydroxide storage solution.

Figures 7A, 7B:
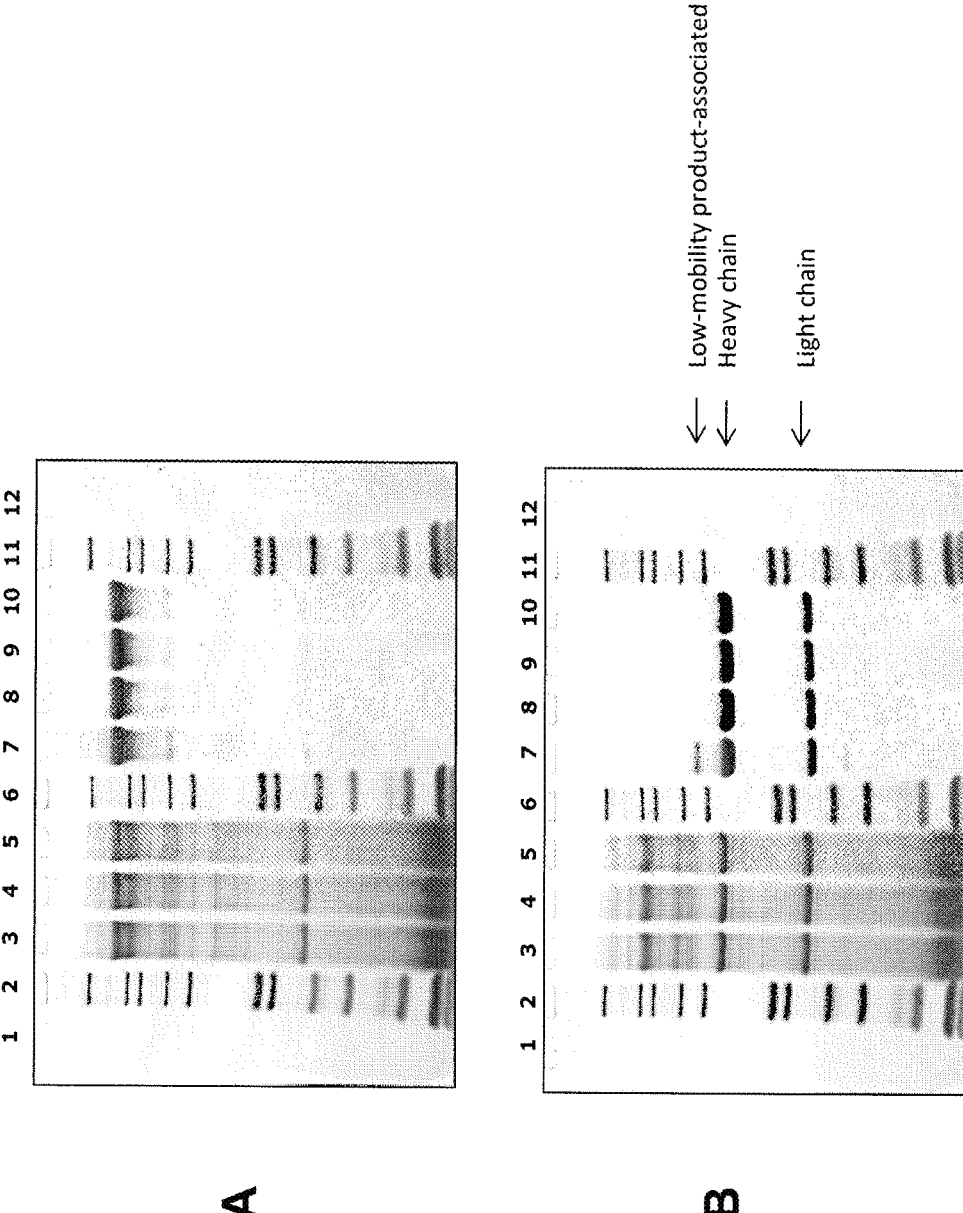
FIG. 7A-B shows stained SDS-PAGE gels run under non-reducing and reducing conditions (FIG. 7 panel A and panel B, respectively) of Ab-A produced in *Pichia.* Purification is observed as reduced levels of product-related impurities in processing from Protein A eluate to CHT pool to PPG HIC pool. In both panels; Lanes 1 and 12: control lanes (X sample buffer); lanes 2, 6 and 11: molecular weight markers; lanes 3-5: total sample loaded onto the Protein A affinity column; lane 7: Ab-A antibody preparation after Protein A affinity chromatography; lane 8: Ab-A antibody preparation after ClHIT chromatography; lane 9; Ab-A antibody preparation after HIC chromatography; and lane 10: Ab-A antibody preparation after bulk filtration (BDS).

Ab-A in the HIC Pool was formulated by ultrafiltration and diafiltration (UFDF) in a tangential flow filtration (TFF) system equipped with 30 kDa molecular weight cut-off membranes. The system was rinsed with water, tested for membrane integrity, sanitized, and equilibrated in a formulation buffer in preparation for loading with 0.2 µm filtered HIC Pool. Following loading, the solution was concentrated by ultrafiltration and then exchanged into formulation buffer by diafiltration versus 6-8 turnover volumes of formulation buffer. The protein solution was further concentrated in a second round of ultrafiltration and then the retentate was drained from the TFF system. The system was flushed with formulation buffer to recover residual protein. The protein concentrations of the retentate and the flush were determined, and then appropriate portions of each were mixed and further adjusted with formulation buffer to achieve the desired final Ab-A concentration. The TFF product was 0.2 µm filtered into sterile bottles in a biological safety cabinet, and stored at $\leq -20°$ C. 100238 Product variants in Ab-A preparations were visualized on protein gels (see FIG. 7). Lanes 1 and 12: control lanes (IX sample buffer): lanes 2, 6 and 11: molecular weight markers; lanes 3-5: total sample loaded onto the Protein A affinity column; lane 7: Ab-A antibody preparation after Protein A affinity chromatography; lane 8: Ab-A antibody preparation after CHT chromatography; lane 9: Ab-A antibody preparation after HIC chromatography; and lane 10: Ab-A antibody preparation after bulk filtration (BDS). Because the samples were subjected to denaturing and reducing conditions (FIG. 7 panel A and panel B, respectively), this method can detect abnormalities affecting the constitution of individual antibody chains but would not be expected to detect other types of abnormalities (such as improper stoichiometry, aggregation, improper disulfide linkages, or other assembly errors). The antibody was purified by Protein-A affinity chromatography, CHT hydroxyapatite mixed mode chromatography and PPG-600M hydrophobic interaction chromatography, as described above, and a sample from different steps along the purification scheme was resolved by SDS-PAGE and stained with Coomassie Blue. The major bands corresponded to the predicted molecular weight of the intact antibody on the non-reduced gel and to heavy and light chains in the reduced gel. Several species of product-associated variants were readily observable in each sample, the most prominent being a low-mobility variant (FIG. 7, arrow labeled "low-mobility product-associated variant"). The low-mobility product-associated variant had decreased electrophoretic mobility relative to the heavy chain. The amount of this product-associated variant was visibly reduced in the antibody preparation following purification using Protein-A affinity chromatography, C-IHT hydroxyapatite mixed mode chromatography and PPG-600M hydrophobic interaction chromatography (sece FIG. 7, compare lanes 3-5 with lanes 7-10).

Antibody purity was also monitored using size-exclusion chromatography. (SE-HPLC) using an Agilent (Santa Clara, CA) 1200 Series HPLC with UV detection instrument. For sample separation, a TSKgel GS3000SWx1 7.8×300 mm column connected with a TSKgel Guard SWxl 6×40 mm from Tosoh Bioscience (King of Prussia, PA) was used. A 100 mM sodium phosphate, 200 mM sodium chloride pH 6.5 was used as mobile phase with a flow rate of 0.5 mL/min in isocratic mode and absorbance at UV 215 nm was monitored. Before injection of samples the column was equilibrated until a stable baseline was achieved. Samples were diluted to a concentration of 1 mg/mL using mobile phase and a 30 µL volume was injected. To monitor column performance, BioRad (Hercules, CA) gel filtration standards were used.

Purification results are presented in Table 4. In particular. Ab-A product as well as low molecular weight (LMW), aggregate and glycovariant (GV) impurities were monitored after Protein-A affinity chromatography, CHT hydroxyapatite mixed mode chromatography, PPG-600M hydrophobic interaction chromatography and UF/DF 30 kDa filter formulation and fill. With every stage of the purification process, there were increasingly reduced levels (%) of each impurity that was monitored, resulting in Ab-A product with at least 98% purity.

TABLE 4

Quantitative assessment of Ab-A purity throughout the purification method. Percentage of aggregate, variant, Ab-A and low-mobility product-associated variant after Protein-A affinity chromatography, CHT hydroxyapatite mixed mode chromatography, PPG-600M hydrophobic interaction chromatography and UP/DF formulation and fill is shown for three different purification preparations of Ab-A.

| | % Aggregate | % Variant | % Ab-A | % Low-molecular weight |
|---|---|---|---|---|
| Purification 1 | | | | |
| Protein A Eluate | 3.6 | 3.8 | 88.5 | 4.2 |
| CHT | 0.6 | 0.7 | 95.4 | 7.5 |
| PPG | 0.3 | 0.6 | 98.2 | 0.9 |
| UFDF Product | 0.1 | 0.6 | 98.1 | 1.2 |
| Purification 2 | | | | |
| Protein A Eluate | 2.1 | 9.6 | 86.9 | 1.4 |
| CHT Pool | 0.6 | 0.7 | 97,7 | 1.1 |
| PPG Pool | 0.2 | 0.6 | 98.4 | 0.8 |
| UFDF Product | 0.2 | 0.6 | 98.3 | 0.9 |
| Purification 3 | | | | |
| Protein A Eluate | 3.4 | 11.8 | 83.1 | 1.7 |
| CHT Pool | 0.2 | 0.7 | 97.8 | 1.4 |
| PPG Pool | 0.4 | 0.7 | 98.1 | 0.8 |
| UFDF Product | 0.2 | 0.7 | 99.1 | 0.1 |

Additional process-related impurity monitoring was performed to quantitate clearance of host cell proteins, residual Protein A, dsDNA and glycans (e.g., l-D-glucan) as a result of purification methods that include a lectin-binding monitoring step. See, Table 5. Overall, the purification scheme resulted in reduced levels of impurities in the purified antibody sample.

TABLE 5

Quantitative assessment of process-related impurity clearance provided by the purification methods. The concentration (relative to antibody) of *P. pastoris* host cell protein (HCP), *S. cerevisiae* host cell protein (HCP), residual Protein A, dsDNA and β-D-glucan after Protein-A affinity chromatography, CHT hydroxyapatite mixed mode chromatography, and PPG-600M hydrophobic interaction chromatography is shown for an exemplary purification preparation of Ab-A.

| | *P. pastoris* HCP ppm | *S. cerevisiae* HCP ppm | Residual Protein A ppm | dsDNA ppm | β-D-glucan ppb |
|---|---|---|---|---|---|
| Protein A | 5,942 | 132 | 8.5 | 1.4 | 19.5 |
| CHT | 2.1 | 9.4 | <0.4 | 3.8 | 16.1 |
| PPG | <1.2 | <2.4 | <0.4 | 2.8 | 16.3 |

Thus, the purification methods including chromatography and lectin-monitoring of impurities demonstrated improved antibody purity. In particular, the final product had greater than 98% purity following Protein-A affinity chromatography, CHT hydroxyapatite mixed mode chromatography and PPG-600M hydrophobic interaction chromatography.

Example 2: Quantitation of Glycoproteins

This example describes a binding assay to facilitate rapid and precise quantitation of glycoproteins in protein samples. These methods can be used to monitor and assess performance of protein expression and protein purification systems. The speed and reproducibility achievable with these methods permit monitoring to occur in near real-time. During protein purification, these methods can be used in multiple ways including identifying fractions which should be collected and optionally pooled, monitoring purification performance, and determining whether a desired level of purity has been achieved or alternatively whether additional or modified purification steps should be performed to achieve the desired level of purity. Similarly, when used to monitor performance of a gene expression system these methods permit feedback control of expression system parameters in order to achieve the desired (e.g., lower) level of glycoproteins.

Strepavidin Biosensors with Biotinylated *Galanthus nivalis* agglutinin were used to determine the concentration of glycovariants in solution relative to a standard. In particular, an Octet interferometer (ForteBio. Menlo Park, CA) with Streptavidin Biosensors (ForteBio) functionalized with biotinylated *Galanthus nivalis* Lectin (GNL [also referred to as GNA], Cat B-1245, Vector Labs. Burlingame, CA) was used to determine the level of activity of a biomolecule in solution relative to a standard. Briefly, sensors were functionalized by pre-wetting in 1× kinetics buffer (a 1:10 dilution in Dulbecco's Phosphate Buffered Saline of 10× kinetics buffer from Fortebio. Part No: 18-5032) then immersed in a dilution of biotinylated GNL lectin and placed on a shaking platform for a prescribed length of time.

Standards, unknowns and controls for measurement were diluted in IX kinetics buffer and arrayed in a black microtiter plate, with replicates as appropriate. The plate with sample dilutions was read on the Octet using the GNL-functionalized sensors and standard quantitation assay methods (such as for Protein A sensors) as described by the manufacturer (ForteBio).

Data Analysis was performed with a ForteBio Analysis software module. Standard curve linearity and reproducibility of known samples were evaluated. Well activity levels were appropriately adjusted for sample concentration/dilution factor to determine mass-normalized specific activity levels, termed Relative Units (RU).

Sample storage and handling: Samples and standards were stored at 4° C. or −20° C. depending on existing stability data. While preparing the assay, samples were kept on ice. Kinetics buffers (Forte Bio Catalog No. 18-5032, 10× and 1×, containing PBS+0.1% BSA, 0.02% Tween20 and 0.05% sodium azide) were stored at 4° C. GNL is stored at 4° C.

Functionalizing the sensors: Strepavidin sensors (Forte Bio Catalog No. 18-5019, tray of 96 biosensors coated with strepavidin) were soaked in 1× Kinetics buffer for at least 5 minutes. Biotinylated GNL was diluted ¹/₁₀₀₀ into 1× kinetics buffer to obtain the volume calculated in step below. 1× kinetics buffer was prepared from 10× kinetics buffer and Hyclone DPBS+Ca+Mg. 120 ul of kinetics buffer was aliquoted per well for each sensor needed into a half area black plate, e.g., 96-Well Black Half Area Plates Medium & High Binding (Greiner Bio-One Cat 675076 or VWR Cat 82050-044). The sensors were transferred to plates with Biotinylated GNL, and the plates were incubated with shaking for at least 30 minutes.

Preparation of the sensors and samples: Sensors were handled with a multichannel pipettor with particular care for the tips of the sensors since damage (e.g., scraping) to these tips can affect the assay results. A medium binding black plate was used for sensors with sensor tray. A separate black plate was used for samples and standards. 150 µl was added per well for unknowns, controls and standards. A media blank or a solution containing a known glycovariant concentration can be optionally included as a control sample. A new sensor was used for each standard well of the assay. Each sensor was rinsed in 1× kinetics buffer before use. A duplicate 3-fold dilution series of 8 points was sufficient for a standard curve. The dilutions were made using 1× kinetics buffer. 1× kinetics buffer was also used as a blank sample.

The Octet conditions were set as follows: Quantitation Time (s) 250; Shake speed 1000 rpm. The plate was defined by assigning the sample wells and the sensors. In particular, the sample wells were assigned by selecting the wells corresponding to the samples and entering their identity, e.g., "unknown" to input a dilution factor or "standard" to input a known concentration. The sensors were not reused for this assay. The program optionally included a delay and/or shaking before processing the sample (e.g., plate was equilibrated to 30° C. while shaking at 200 RPM for 300 seconds).

A different lectin, DC-SIGN (R&D Systems cat #161-DC-050) was biotinylated with LC-LC-biotin (Pierce cat #21338) and used to functionalize streptavidin sensors that were employed in a similar assay as described above.

The Octet lectin-binding assay described above was used to quantitate the amount of glycosylated proteins present in fractions of the eluate collected after hydroxyapatite mixed mode chromatography and after hydrophobic interaction chromatography. In particular, Octet Activity (RU) values for binding to GNA and DC-SIGN were determined for each of 21 fractions of the eluate collected after CHT hydroxyapatite mixed mode chromatography and for each of 25 fractions of the eluate collected after PPG-600M hydrophobic interaction chromatography. See, FIG. 5, panel A and FIG. 6, panel A, respectively. For each fraction analyzed, the Octet Activity (RU) value was plotted against the concentration of Ab-A present in the same fraction. For CHT fractions, both GNA Octet values and DC-SIGN Octet values correlated well with relative glycovariant concentration. See, FIG. 4.

Fractions of the column eluate were selected for further processing based on the level of glycovariant impurities contained in the sample as determined using the Octet assays using either Baseline pooling criteria or strict pooling criteria discussed in Example 1. In particular, following strict pooling criteria, fraction 1 through fraction 10 of the CHT hydroxyapatite mixed mode column were selected for further processing, whereas fraction 1 through fraction 13 were selected for further processing per Baseline pooling criteria. The strict pooled fractions had a 1.9 RU, compared to a 2.3 RU for the Baseline pooled fractions, as determined by GNA-Octet assay. The glycovariant impurity content as measured by Octet assay correlated with increased levels of monomannose, mannobiose and mannotriose in the Baseline criteria pool compared to the strict criteria pool (i.e., 1.55 mol monomannose/mol Ab-A in the Stringent Pool compared to 1.60 mol monomannose/mol Ab-A in the Baseline Pool, and 0.22 mol mannotriose/mol Ab-A in the Stringent Pool compared to 0.28 mol mannotriose/mol Ab-A in the Baseline Pool). See, FIG. 5, panel B.

Similarly, following strict pooling criteria, fraction 8 through fraction 23 of the PPG-600M hydrophobic interaction column were selected for further processing, whereas fraction 4 through fraction 23 were selected for further processing per Baseline pooling criteria. The strict pooled fractions had a 1.1 RU, compared to a 1.4 RU for the Baseline pooled fractions, as determined by GNA-Octet assay. The glycovariant impurity content as measured by Octet assay correlated with increased levels of monomannose, mannobiose and mannotriose in the Baseline criteria pool compared to the strict criteria pool (i.e., 1.57 mol monomannose/mol Ab-A in the Stringent Pool compared to 1.48 mol monomannose/mol Ab-A in the Baseline Pool: 0.52 mol mannobiose/mol Ab-A in the Stringent Pool compared to 0.14 mol mannobiose mol/Ab-A mol in the Baseline Pool; and 0.32 mol mannotriose/mol Ab-A in the Stringent Pool compared to 0.07 mol mannotriose/mol Ab-A in the Baseline Pool). See, FIG. 6, panel B.

Thus, the quantitative lectin binding assay when used in combination with chromatographic purification methods improves antibody product purity. Based on the level of lectin-binding activity, particular fractions of the eluate after different chromatography steps can be selected for further processing to increase the yield of the desired antibody product and minimize the presence of unwanted impurities.

Example 3: Ab-B Purification and Recovery

This example illustrates that the purity of recombinant antibodies generated in P. pastoris was improved by using a series of primary recovery and chromatographic purification processes. An overview of the purification method is shown in FIG. 1. These methods can be used to purify and recover a variety of antigen-specific antibodies expressed in different systems.

P. pastoris cells containing stably integrated sequences encoding the Ab-B heavy and light chains (corresponding to SEQ ID NO:681 and SEQ ID NO:701 as listed in US 20120294797, which is incorporated by reference in its entirety) were cultured and antibody expression was induced.

Whole broth was treated with ethylene diamine tetraacetic acid (EDTA) to 3 mM final concentration and with a flocculating agent. Cells and flocculated debris were removed from the harvested broth by centrifugation, and followed by clarification through depth and 0.2 µm filters.

The clarified broth was applied to a column of MabSelect SuRe resin to capture Ab-B by Protein A affinity chromatography. Chromatography was performed at ambient temperature. A column of 23 cm bed height was sanitized with 0.1 M sodium hydroxide and then equilibrated with 20 mM sodium phosphate, 150 mM sodium chloride, pH 6.0 buffer ("Pr A equilibration buffer") prior to loading. The column was loaded to a target capacity of 25 g Ab-B per L resin at 250 cm/hr linear velocity, and then operated at the same linear velocity throughout. Following application of the load, the column was rinsed for ≥3 column volumes (CV) with capture equilibration buffer to remove loosely bound materials. Bound Ab-B was then desorbed with ≥3 CV of 1 M arginine, pH 4.0 elution buffer ("PrA elution buffer"). The $OD_{280}$ of the effluent was monitored, and eluate was collected from 1 OD on the front flank to 1 OD on the rear flank. The eluate was collected in a vessel pre-loaded with 0.15 CV of 1 M Tris. pH 8.0 neutralization buffer ("PrA neutralization buffer"). Following collection the vessel's contents were mixed, and its pH value determined, prior to final adjustment to pH 6.5 using either 5% hydrochloric acid or 1 M sodium hydroxide as necessary. The neutralized eluate was 0.2 μm filtered, then forwarded on to the hydroxyapatite chromatography step. Following product elution, the Protein A column was cleaned with 0.2 M sodium hydroxide for 3CV, and rinsed with equilibration buffer for 3 CV prior to storage in 20% ethanol.

Intermediate purification of Ab-B uses mixed mode chromatography on ceramic hydroxyapatite (CHT, Type 1, 40 μm) resin. This step was carried out at ambient temperature and at not more than 200 cm/hr linear velocity throughout. Prior to running, the column was sanitized using 3 CV of 1 M sodium hydroxide and equilibrated with at least 3 CV 5 mM sodium phosphate, pH 6.5 equilibration buffer ("CHT equilibration buffer"). The CHT load was prepared by diluting the filtered, neutralized capture eluate with CHT equilibration buffer to a conductivity of not more than 4 mS/cm. The CHHT load was then applied to the equilibrated column after passing through a 0.2 μm filter. Following loading, the column was washed with 5 CV of equilibration buffer and then eluted with a 20 CV linear gradient from 5 mM to 0.25 M sodium phosphate, pH 6.5 ("CHT elution buffer 2"). The $OD_{280}$ of the effluent was monitored, and a series of fractions of ~½ CV were collected from 0.1 OD on the front flank to 0.1 OD on the rear flank. The fractions were analyzed for purity, and a set of contiguous fractions were combined to achieve a CHT Pool of desired purity and reduced glycovariant content (see FIG. 8). After elution, the CHT column was stripped with 5 CV 500 mM sodium phosphate. pH 6.5 strip buffer ("CHT strip buffer"), cleaned in place with 5 CV 1 M sodium hydroxide, and rinsed with 5 CV 20% ethanol storage solution.

Polish purification of Ab-B used hydrophobic interaction chromatography (HIC) on Phenyl High Performance (GE Healthcare) resin. This step was carried out at ambient temperature and at not more than 200 cm/hr linear velocity throughout. Prior to running, the column was sanitized using 3 CV of 1 M sodium hydroxide, and equilibrated with 5CV 20 mM sodium phosphate, 0.7 M sodium sulfate, pH 7.0 equilibration buffer ("HIC equilibration buffer"). The HIC load was prepared by adjusting 0.2 μm filtered CHT Pool to a conductivity ≥77.5 mS/cm using 20 mM sodium phosphate. 1.1 M sodium sulfate. pH 7.0 HIC dilution buffer. The HIC load was then applied to the equilibrated column after passing through a 0.2 μm filter. Following loading, the column was washed with 5 CV of HIC equilibration buffer and then eluted with a 20 CV linear gradient from 0-100%

20 mM sodium phosphate, pH 7.0 ("HIC elution buffer"). The $OD_{280}$ of the effluent was monitored, and a series of fractions of ~⅓$^{rd}$CV were collected from 0.1 OD on the front flank to 0.1 OD on the rear flank. The fractions were analyzed for purity (see FIG. 9), and a set of contiguous fractions were combined to form a HIC Pool of desired purity and reduced glycovariant content (see FIG. 8 and FIG. 9). After elution, the HIC column was stripped with 4 CV HIC elution buffer, cleaned in place with ≥3 CV 1 M sodium hydroxide, and transferred into 0.1 M sodium hydroxide storage solution.

Product variants in Ab-B preparations were visualized on protein gels (see FIG. 10). In both gels, lanes 1, 2 and 6 contain molecular weight markers; lane 3 contains Protein A eluate; lane 4 contains CHT pool; and lane 5 contains HIC pool. Because the samples were subjected to denaturing and reducing conditions (FIG. 10 panel A and panel B, respectively), this method can detect abnormalities affecting the constitution of individual antibody chains but would not be expected to detect other types of abnormalities (such as improper stoichiometry, aggregation, improper disulfide linkages, or other assembly errors). The antibody was purified by Protein-A affinity chromatography. CHT hydroxyapatite mixed mode chromatography and Phenyl-Sepharose High Performance (HP) hydrophobic interaction chromatography, as described above, and a sample from different steps along the purification scheme was resolved by SDS-PAGE and stained with Coomassie Blue. The major bands corresponded to the predicted molecular weight of the intact antibody on the non-reduced gel and to heavy and light chains in the reduced gel. Several species of product-associated variants were readily observable in each sample, the most prominent being a low-mobility variant (FIG. 10, arrow labeled "low-mobility product-associated variant"). The low-mobility product-associated variant had decreased electrophoretic mobility relative to the heavy chain. The amount of this product-associated variant was visibly reduced in the antibody preparation following purification using Protein-A affinity chromatography, CHT hydroxyapatite mixed mode chromatography and Phenyl HIP hydrophobic interaction chromatography (see FIG. 10, compare lanes 4-5 with lane 3).

Antibody purity was also monitored using size-exclusion chromatography. (SE-HPLC) using an Agilent (Santa Clara, CA) 1200 Series HPLC with IUV detection instrument. For sample separation, a TSKgel GS3000SWx1 7.8×300 mm column connected with a TSKgel Guard SWx1 6×40 mm from Tosoh Bioscience (King of Prussia, PA) was used. A 100 mM sodium phosphate, 200 mM sodium chloride pH 6.5 was used as mobile phase with a flow rate of 0.5 mL/min in isocratic mode and absorbance at UV 215 nm was monitored. Before injection of samples the column was equilibrated until a stable baseline was achieved. Samples were diluted to a concentration of 1 mg/mL using mobile phase and a 30 μL volume was injected. To monitor column performance. BioRad (Hercules, CA) gel filtration standards were used.

Purification results are presented in Table 6. In particular, Ab-B product as well as low molecular weight (LMW), aggregate and glycovariant (GV) impurities were monitored after Protein-A allinity chromatography, CHT hydroxyapatite mixed mode chromatography, Phenyl HP hydrophobic interaction chromatography. With every stage of the purification process, there were increasingly reduced levels (%) of each impurity that was monitored, resulting in Ab-B product with at least 95% purity.

55

TABLE 6

Quantitative assessment of Ab-B purity throughout the purification
method. Percentage of aggregate, variant, Ab-B and low-mobility
product-associated variant after Protein-A affinity chromatography,
CHT hydroxyapatite mixed mode chromatography, and Phenyl
HP hydrophobic interaction chromatography is shown for an
exemplary purification preparation of Ab-B.

| | % Aggregate | % Variant | % Ab-A | % Low-molecular weight |
|---|---|---|---|---|
| Protein A | 9.8 | 14.2 | 72.3 | 3.8 |
| CHT | 0.0 | 7.9 | 87.9 | 4.2 |
| Phenyl HP | 0.0 | 0.0 | 95.6 | 4.3 |

Additional process-related impurity monitoring was performed to quantitate clearance of host cell proteins, residual Protein A, dsDNA and glycans (e.g., ß-D-glucan) as a result of purification methods that include a lectin-binding monitoring step. See, Table 7. Overall, the purification scheme resulted in reduced levels of impurities in the purified antibody sample.

TABLE 7

Quantitative assessment of process-related impurity clearance
provided by the purification methods. The concentration (relative
to antibody) of P. pastoris host cell protein (HCP), S. cerevisiae
host cell protein (HCP), residual Protein A, dsDNA and β-D-glucan
after Protein-A affinity chromatography, CHT hydroxyapatite
mixed mode chromatography, and Phenyl HP hydrophobic interaction
chromatography is shown for Ab-B.

| | P. pastoris HCP ppm | S. cerevisiae HCP ppm | Residual Protein A ppm | dsDNA ppm | β-D-glucan ppb |
|---|---|---|---|---|---|
| Protein A | 2,314 | 126 | 6.1 | 2.4 | 5.8 |
| CHT | 282 | 57 | <0.4 | 2.8 | 2.0 |
| Phenyl HP | 21 | 3.7 | <0.4 | 1.5 | 7.8 |

Thus, the chromatographic purification methods demonstrated improved antibody purity. In particular, the final product had greater than 95% purity following Protein-A affinity chromatography, CHT hydroxyapatite mixed mode chromatography and Phenyl-HP hydrophobic interaction chromatography. In addition, the lectin binding assay performed on process intermediates demonstrated that the described purification process led to purified Ab-B with reduced GNA binding activity (see, FIG. 8). The lectin binding assay performed on pools of HIC fractions demonstrated that selection of appropriate HIC elution fractions to combine may lead to a HIC Pool with reduced GNA binding activity, by exclusion of other fractions that have higher GNA binding activity (see, FIG. 9).

Example 4: Ab-C Fab Purification and Recovery

This example demonstrates that the lectin-binding assay disclosed herein may be used to detect glycosylation impurities of recombinant antibody fragments generated in in P. pastoris.

P. pastoris cells containing stably integrated sequences encoding the Ab-C Fab were cultured and expression of the antibody fragment was induced. Alternatively, the Ab-C Fab can be produced chemically by proteolysis of the full-length Ab-C expressed antibody.

Briefly, clarified culture supernatant was contacted on a mixed mode resin at a low pH and low conductivity, washed, and then eluted with a gradient strategy that employed raising the pH and conductivity simultaneously. Eluted fractions were monitored for quality and appropriate fractions pooled and buffer exchanged into a final buffer. In particular, fractions were monitored for glycosylation impurities (RU) using the GNA lectin assay described above.

Antibody fragment purity was also monitored using size-exclusion chromatography. (SE-HPLC) using an Agilent (Santa Clara. CA) 1200 Series HPLC with UV detection instrument. For sample separation, a TSKgel GS3000SWx1 7.8×300 mm column connected with a TSKgel Guard SWx1 6×40 mm from Tosoh Bioscience (King of Prussia, PA) was used. A 100 mM sodium phosphate, 200 mM sodium chloride pH 6.5 was used as mobile phase with a flow rate of 0.5 ml/min in isocratic mode and absorbance at UV 215 nm was monitored. Before injection of samples the column was equilibrated until a stable baseline was achieved. Samples were diluted to a concentration of 1 mg/mL using mobile phase and a 30 μL volume was injected. To monitor column performance, BioRad (Hercules, CA) gel filtration standards were used.

Purification results are presented in Table 8. In particular. Ab-C Fab product as well as low molecular weight (LMW), aggregate and glycovariant (GV) impurities were monitored after mixed mode chromatography using size-exclusion chromatography. Additionally, glycosylated impurities were detected using the GNA lectin assay. The purification resulted in Ab-C Fab product with about 90% purity.

TABLE 8

Quantitative assessment of Ab-C Fab purity throughout the purification
method. Percentage of aggregate, variant, Ab-C Fab and low-mobility
product-associated variant after mixed mode chromatography is
shown for an purification preparation of Ab-C Fab.

| Purified Protein | RU | % Aggregate | % Variant | % Ab-C Fab | % Low-molecular weight |
|---|---|---|---|---|---|
| Ab-C Fab | 11.5 | 6.8 | 3.1 | 89.9 | 0.2 |

Thus, the purification methods including chromatography and lectin-monitoring of impurities demonstrated Fab antibody fragment purity. In particular, the final product had greater than 90% purity following mixed mode chromatography.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

The invention may be practiced in ways other than those particularly described in the foregoing description and examples. Numerous modifications and variations of the invention are possible in light of the above teachings and, therefore, are within the scope of the appended claims.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

Certain teachings related to methods for obtaining a clonal population of antigen-specific B cells were disclosed in U.S. Provisional patent application No. 60/801,412, filed May 19, 2006, and U.S. Patent Application Pub. No. 2012/0141982, the disclosure of each of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006. (U.S. Patent Application Publication No. US2006/0270045), the disclosure of which is herein incorporated by reference in its entirety.

The entire disclosure of each document cited herein (including patents, patent applications, journal articles, abstracts, manuals, books, or other disclosures), including each document cited in the Background. Summary, Detailed Description, and Examples, is hereby incorporated by reference herein in its entirety.

What is claimed is:

1. A collection of humanized antibody containing samples, (a) each comprising a protein A eluate comprising:

(1) a humanized antibody comprising a heavy chain having the amino acid sequence of SEQ ID NO: 54 and a light chain having the amino acid sequence of SEQ ID NO: 52;

(2) a glycovariant of said humanized antibody which glycovariant is comprised in the samples in an amount of 1% to less than 10%; and (3) one or more antibody aggregates which are present in the samples in an amount of 1% to less than 3%;

wherein each sample (a) is derived from a fermentation medium of a *Pichia pastoris* culture which comprises *Pichia pastoris* cells, which have each been engineered with a genetic construct that comprises a nucleic acid which encodes for the humanized antibody, and which construct provides for expression and secretion of said humanized antibody into the fermentation medium by said *Pichia pastoris* cells and further results in production of and secretion of said glycovariant and said antibody aggregates into the fermentation medium comprising said *Pichia pastoris* cells; wherein:

(i) the different samples (a) are selected from a larger set of samples (b), which are each obtained from the fermentation medium of different *Pichia pastoris* cultures which have each been engineered with a genetic construct that comprises a nucleic acid which encodes for said humanized antibody, which construct provides for the expression and secretion of said humanized antibody into the fermentation medium by said *Pichia pastoris* cells; wherein the cultures used to obtain the samples of (b) have been cultured under fermentation conditions that result in the expression and secretion of said humanized antibody and said glycovariant and said antibody aggregates into the fermentation medium;

(ii) a specific subset of samples (a) is selected from (b) for use in purification steps that provide for the removal of said glycovariant and antibody aggregates from the samples.

2. The collection of different samples (a) of claim 1, wherein the glycovariant of said humanized antibody is the result of O-linked glycosylation.

3. The collection of different samples (a) of claim 1, wherein:

(i) the samples (a) each comprise less than 50 ng/mg of said glycovariant;

(ii) the samples (a) each comprise less than 25 ng/mg of said glycovariant; or (iii) the samples (a) each comprise less than 10 ng/mg of said glycovariant.

4. The collection of different samples (a), of claim 1, wherein said larger set of samples (b) have been contacted with at least one chromatographic support comprising Protein A prior to selection of said specific subset of samples (a) for purification steps that provide for the removal of said glycovariant and said antibody aggregates.

5. A second collection of humanized antibody samples, each comprising a hydroxyapatite eluate comprising:

(1) the humanized antibody comprised in the samples in an amount of greater than or equal to 91%;

(2) the glycovariant of said humanized antibody which glycovariant is comprised in the samples in an amount of 0.5% to less than or equal to 1.0%; and (3) said antibody aggregates which are present in the samples in an amount less than 1%;

wherein the second collection of humanized antibody samples is formed by subjecting the first collection of humanized antibody samples (a) of claim 1 to a chromatographic support comprising a ceramic hydroxyapatite.

6. A third collection of humanized antibody samples, each comprising a hydrophobic interaction chromatography eluate comprising:

(1) the humanized antibody comprised in the samples in an amount of at least 95%;

(2) the glycovariant of said humanized antibody which glycovariant is comprised in the samples in an amount of 0.5% to less than 1%; and (3) one or more antibody aggregates which are present in the samples in an amount less than 1%;

wherein the third collection of humanized antibody samples is formed by subjecting the second collection of humanized antibody samples of claim 5 to a chromatographic support comprising polypropylene glycol PPG-600M.

7. The third collection of humanized antibody samples of claim 6, wherein:

(i) the samples each comprise less than 50 ng/mg of said glycovariant;

(ii) the samples each comprise less than 25 ng/mg of said glycovariant;

(iii) the samples each comprise less than 10 ng/mg of said glycovariant.

* * * * *

SEQUENCE LISTING

```
<160> NUMBER OF SEQ ID NOS: 54

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
```

-continued

```
<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20
```

-continued

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

-continued

```
<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000
```

```
<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30
```

-continued

```
Tyr Leu Ala Trp Tyr Gln Gln Lys Pro Gly Lys Val Pro Lys Gln Leu
    35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 53

<400> SEQUENCE: 53

000

<210> SEQ ID NO 54
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
                20                  25                  30

Tyr Met Asn Trp Val Arg Gln Ala Pro Gly Lys Gly Leu Glu Trp Val
            35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
```

-continued

```
        130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Ala Arg
                195                 200                 205

Val Glu Pro Lys Ser Cys Asp Lys Thr His Thr Cys Pro Pro Cys Pro
            210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440
```